United States Patent [19]
Haissaguerre et al.

[11] Patent Number: 6,068,629
[45] Date of Patent: May 30, 2000

[54] SYSTEM AND METHODS FOR TISSUE MAPPING AND ABLATION

[75] Inventors: Michel Haissaguerre, Talence, France; Walter Bruszewski, San Francisco, Calif.; Le Le; Mark Maguire, both of San Jose, Calif.; John Gaiser, Mountain View, Calif.; Huu Nguyen, San Jose, Calif.

[73] Assignee: Medtronic, Inc., Minneapolis, Minn.

[21] Appl. No.: 09/213,332

[22] Filed: Dec. 15, 1998

Related U.S. Application Data

[62] Division of application No. 08/794,804, Feb. 4, 1997, Pat. No. 5,916,213.

[51] Int. Cl.$^7$ ................................................. A61B 17/39
[52] U.S. Cl. ............................ 606/41; 606/47; 607/122; 600/374
[58] Field of Search ............................ 128/898; 600/373, 600/32, 41, 46, 47, 374, 375, 377, 381; 607/122, 119, 101

[56] References Cited

U.S. PATENT DOCUMENTS

| | | |
|---|---|---|
| 4,057,067 | 11/1977 | Lajos . |
| 4,112,952 | 9/1978 | Thomas et al. . |
| 4,332,259 | 6/1982 | McCorkie, Jr. . |
| 4,458,677 | 7/1984 | McCorkie, Jr. . |
| 4,567,901 | 2/1986 | Harris . |
| 4,660,571 | 4/1987 | Hess et al. ................................ 600/374 |
| 5,327,889 | 7/1994 | Imran . |
| 5,396,887 | 3/1995 | Imran . |
| 5,409,000 | 4/1995 | Imran . |
| 5,431,683 | 7/1995 | Bowald et al. . |
| 5,439,485 | 8/1995 | Mar et al. . |
| 5,476,495 | 12/1995 | Kordis et al. . |
| 5,487,757 | 1/1996 | Truckai et al. . |
| 5,569,241 | 10/1996 | Edwards . |
| 5,626,136 | 5/1997 | Webster, Jr. . |
| 5,657,755 | 8/1997 | Desai ...................................... 607/122 |
| 5,680,860 | 10/1997 | Imran . |
| 5,730,127 | 3/1998 | Avitali . |

FOREIGN PATENT DOCUMENTS

| | | |
|---|---|---|
| WO 95/34346 | 12/1995 | WIPO . |
| WO 96/00036 | 1/1996 | WIPO . |
| WO 96/26675 | 9/1996 | WIPO . |

*Primary Examiner*—Linda C. M. Dvorak
*Assistant Examiner*—David Ruddy
*Attorney, Agent, or Firm*—Daniel W. Latham; Harold R. Patton

[57] ABSTRACT

A steerable electrophysiology catheter includes a shaft having a distal ablation segment with one or more electrodes coupled to a source of electrical energy by a connector extending through the shaft. The distal ablation segment of the shaft is movable between a collapsed configuration sized for percutaneous introduction into the patient and/or endoluminal delivery to the target site and an expanded configuration, in which the distal ablation segment forms a substantially continuous surface transverse to the shaft axis for engaging the heart tissue and creating a linear lesion thereon. The catheter includes one or more force element(s) positioned to apply an axial force between the distal and proximal ends of the ablation segment. The force element(s) provide a sufficiently uniform force against the distal ablation segment to establish continuous contact pressure between the electrodes and the patient's heart tissue. This contact pressure allows the surgeon to engage the entire length of the distal ablation segment against the heart tissue to provide a relatively long linear lesion on this tissue.

21 Claims, 25 Drawing Sheets

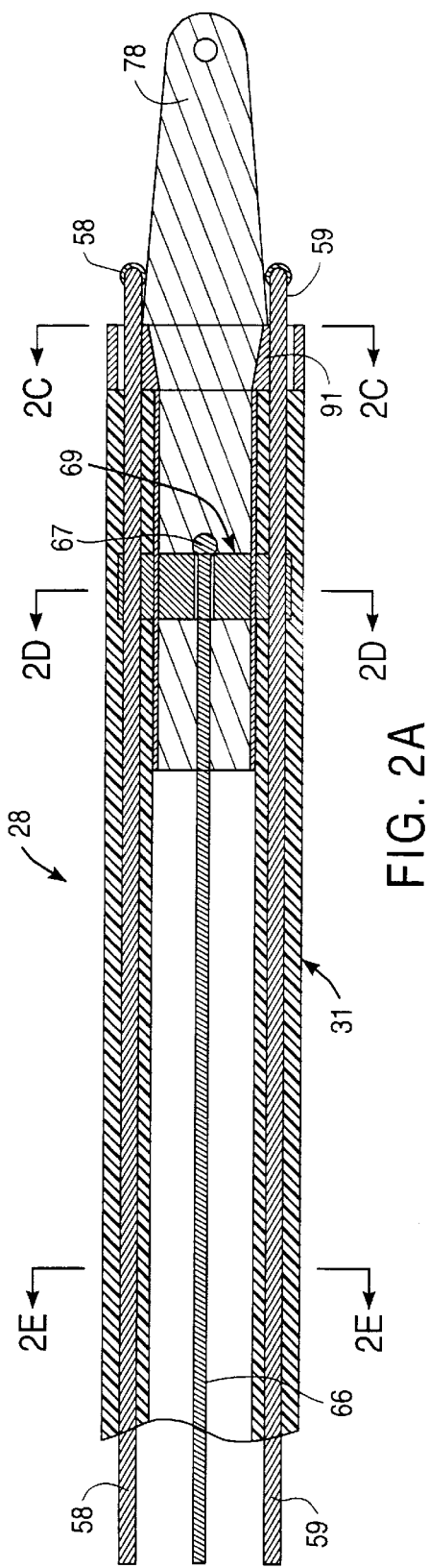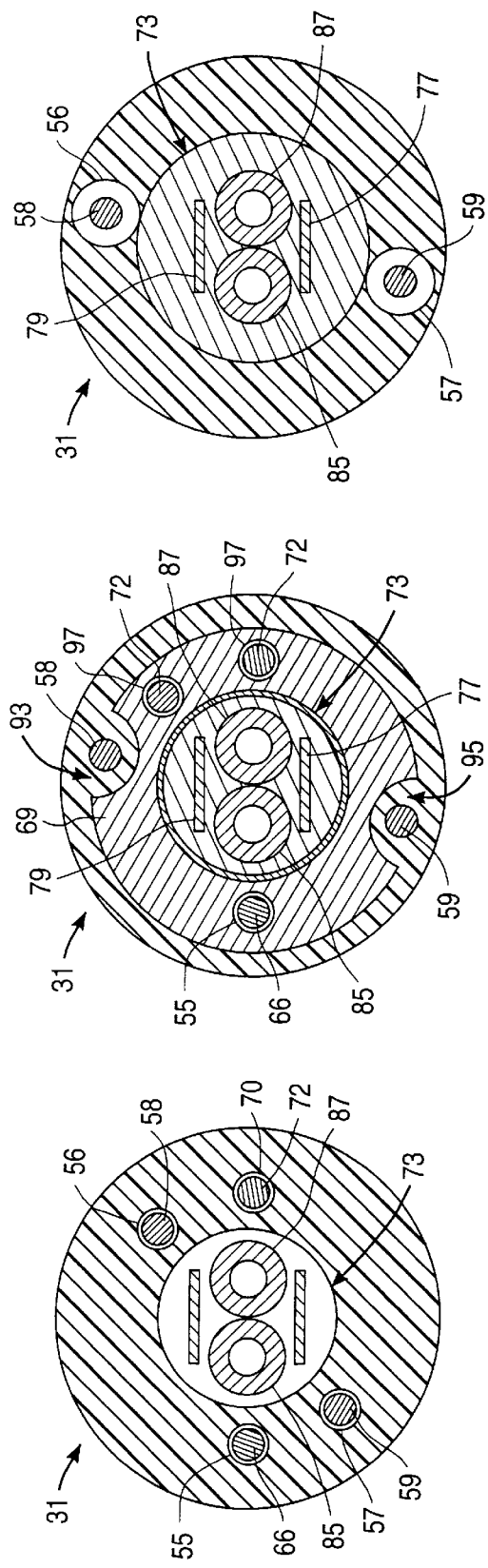

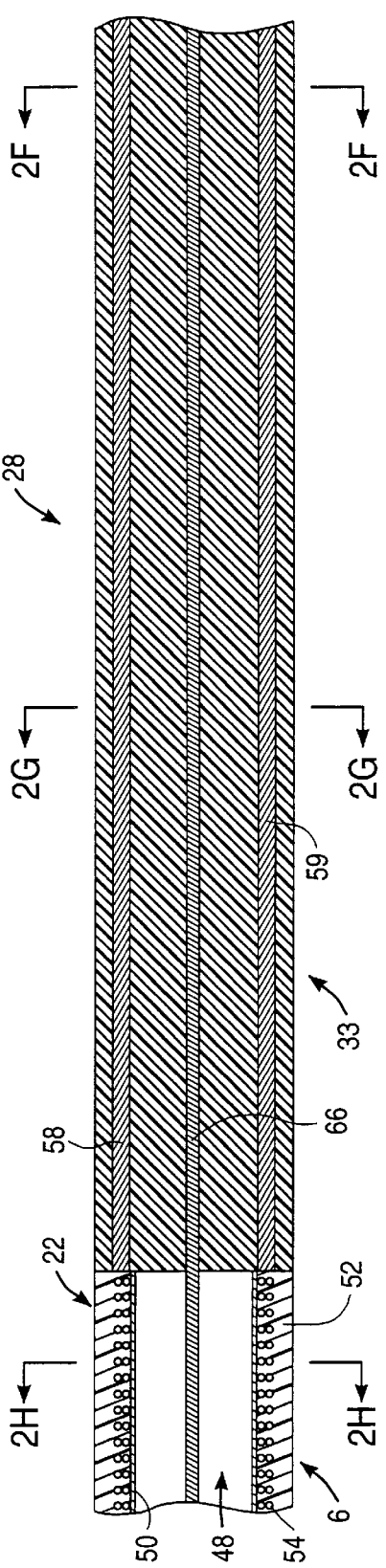
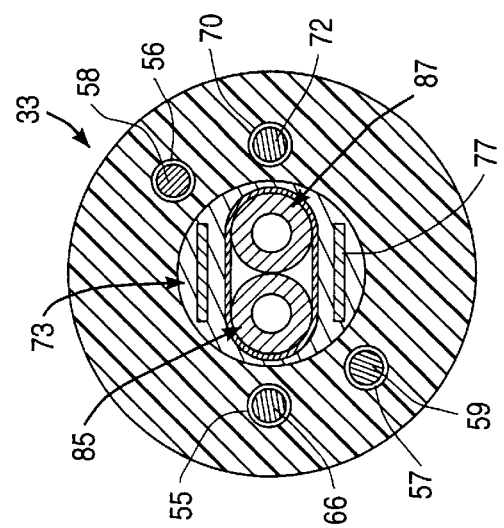
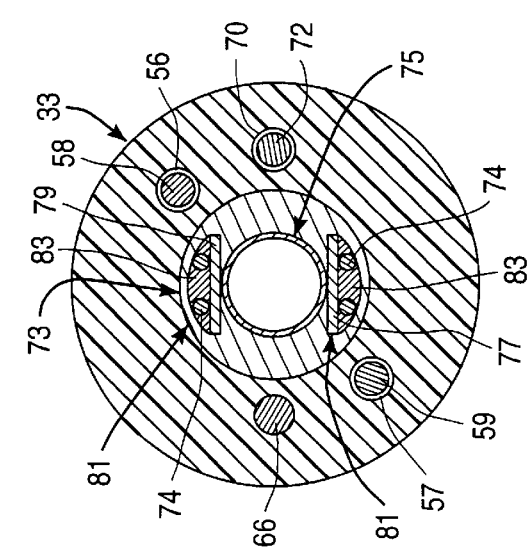
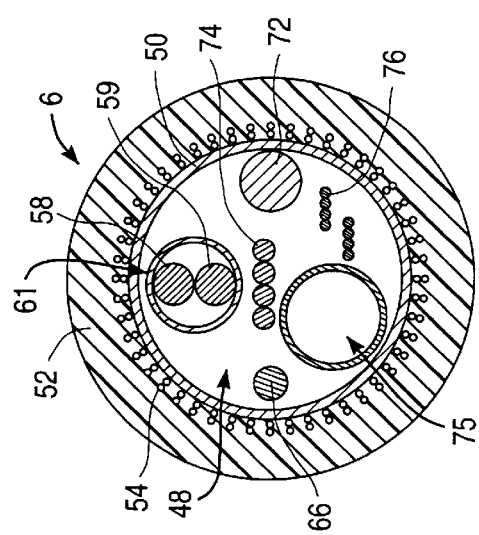
FIG. 2B
FIG. 2F
FIG. 2G
FIG. 2H

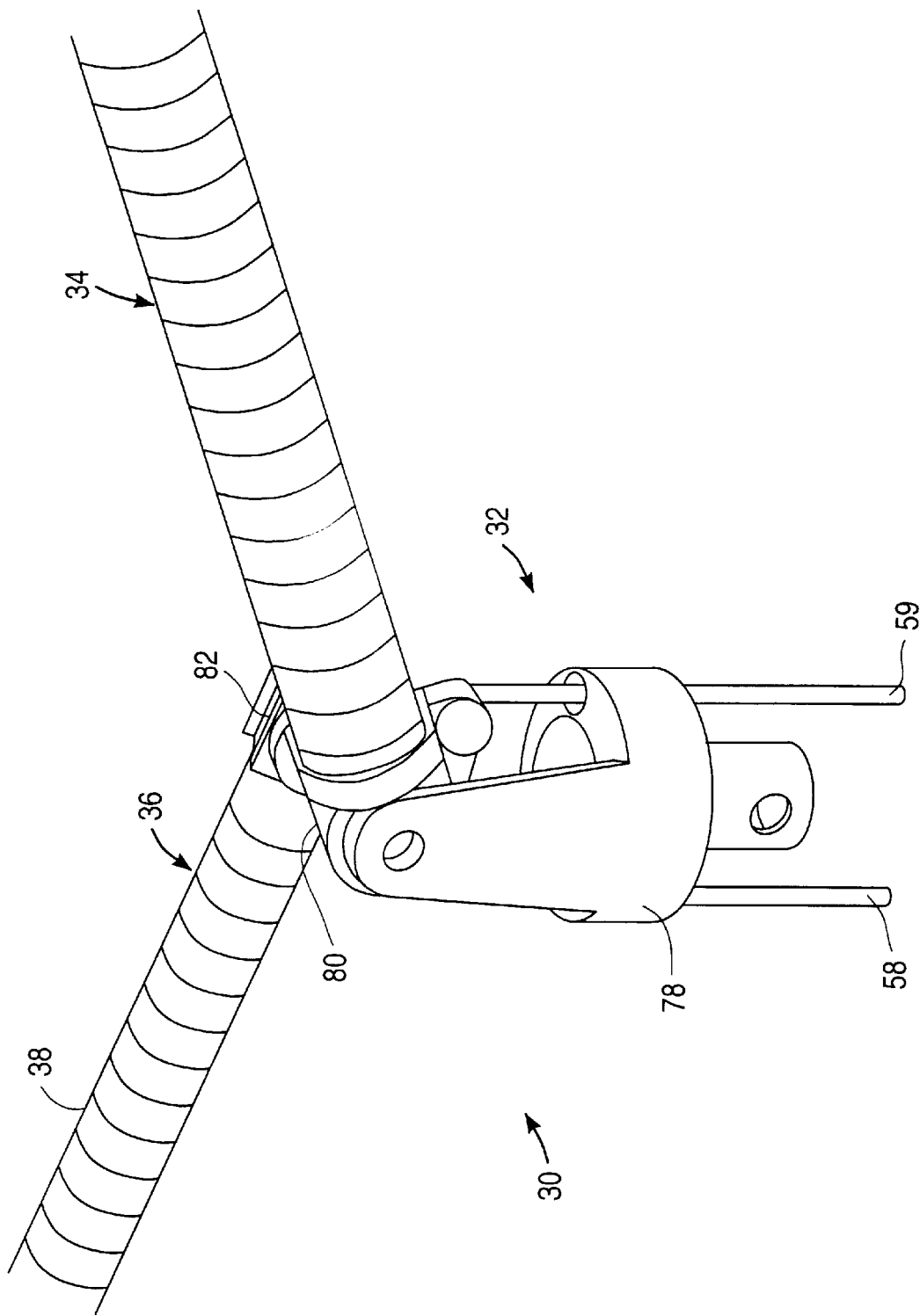

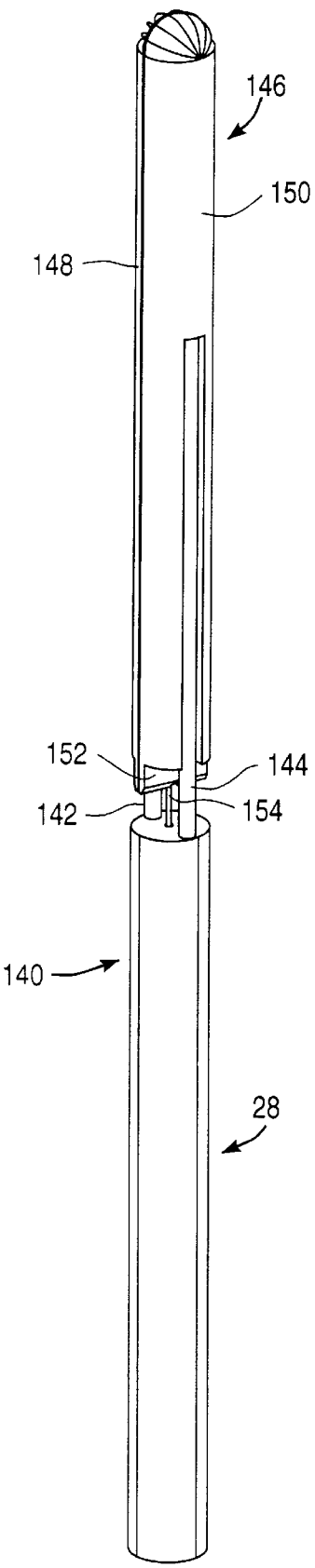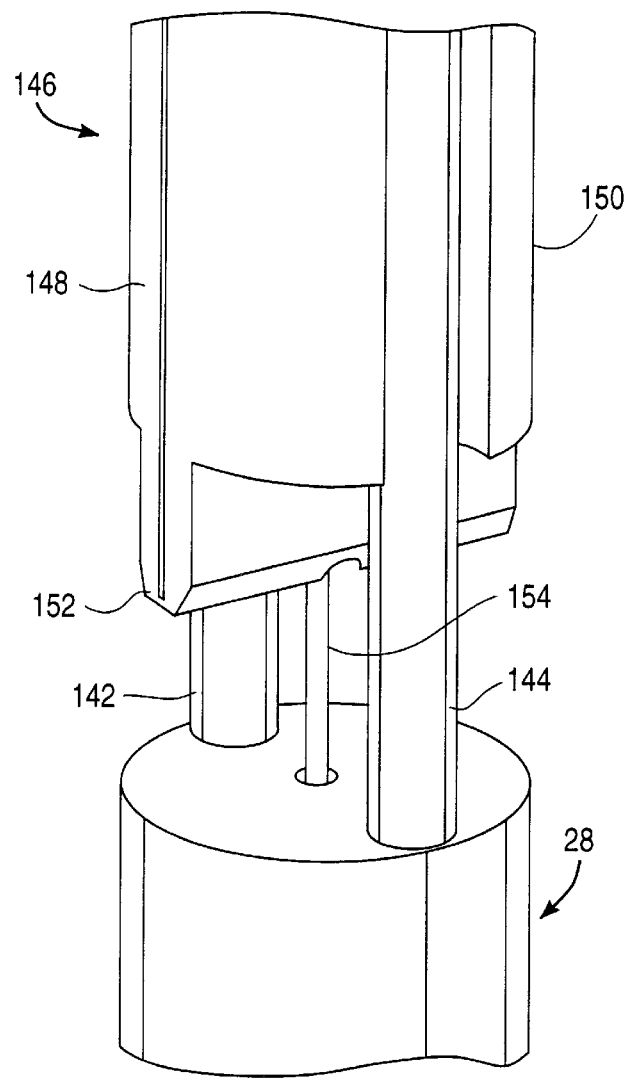
FIG. 14A
FIG. 14B

SYSTEM AND METHODS FOR TISSUE MAPPING AND ABLATION

CROSS-REFERENCE TO RELATED APPLICATIONS

This application is a divisional application of patent application Ser. No. 08/794,804 filed Feb. 4, 1997, now U.S. Pat. No. 5,916,213. This application is also related to commonly assigned patent application Ser. No. 08/794,066 entitled "Linear Ablation Catheter", now U.S. Pat. No. 5,919,188, and patent application Ser. No. 08/794,803 entitled "Fluid Cooled Ablation Catheter and Method for Making", now U.S. Pat. No. 5,913,854. The complete disclosure of any and all patents, patent applications and printed publications referred to herein are incorporated by reference.

BACKGROUND OF THE INVENTION

The present invention relates generally to systems and methods for applying electrical energy to a patient and more specifically to steerable electrophysiology catheters for use in mapping and/or ablation of the heart.

The heart is primarily composed of multiple fibers which are responsible for the propagation of signals necessary for normal, electrical and mechanical function. The presence of an arrhythmogenic site or abnormal pathway which may bypass or short circuit the normal conducting fibers in the heart often causes abnormally rapid rhythms of the heart, which are referred to as tachycardias. Tachycardias may be defined as ventricular tachycardias (VTs) and supraventricular tachycardias (SVTs). VTs originate in the left or right ventricle and are typically caused by arrhythmogenic sites associated with ventricular myocardial disease. SVTs originate in the atria or the atrioventricular (AV) junction and are frequently caused by abnormal circuits or foci.

The present invention is concerned with the treatment of atrial fibrillation and atrial flutter, which are two of the most common sustained cardiac arrhythmias and of the major causes of systemic embolism. Therapy for patients suffering from atrial fibrillation usually focuses on controlling the symptoms (palpitations, angina, dyspnea, syncope and the like), improving cardiac performance and reducing the risk of thromboembolism. Treatment of atrial fibrillation may be accomplished by a variety of approaches, including drugs, surgery, implantable pacemakers/defibrillators, and catheter ablation. While antiarrhythmic drugs may be the treatment of choice for many patients, these drugs may only mask the symptoms and do not cure the underlying cause. Implantable devices, on the other hand, usually can correct an arrhythmia only after it occurs. Surgical and catheter-based treatments, by contrast, may actually cure the problem usually by ablating the abnormal arrhythmogenic tissue or abnormal pathway responsible for the atrial fibrillation or flutter. The catheter-based treatments rely on the application of various destructive energy sources to the target tissue including direct current electrical energy, radiofrequency electrical energy, microwave energy laser energy, cryoenergy, ultrasound and the like.

Of particular interest to the present invention are radiofrequency (RF) ablation protocols which have proven to be effective in treatment of atrial fibrillation while exposing the patient to minimum side effects and risks. Radiofrequency catheter ablation may be performed after an initial mapping procedure where the locations of the arrhythmogenic sites and abnormal pathways are determined. A catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the abnormal pathway. By successfully destroying that tissue, the abnormal conducting patterns responsible for the atrial fibrillation or flutter cannot be sustained. Methods and systems for performing RF ablation by controlling temperature at the ablation site are described in co-pending application Ser. No. 07/866,683, now U.S. Pat. No. 5,573,533 entitled "Method and System for Radiofrequency Ablation of Cardiac Tissue," filed Apr. 10, 1992, the complete disclosure of which is hereby incorporated by reference.

Catheters designed for mapping and/or ablation frequently include a number of individual electrode bands mounted to the distal tip of the catheter so as to facilitate mapping of a wider area in less time, or to improve access to target sites for ablation. Such catheters are described in co-pending application Ser. No. 07/866,383, now U.S. Pat. No. 5,318,525 filed Apr. 10, 1992, the complete disclosure of which is hereby incorporated by reference. Catheters utilized in radiofrequency ablation are typically inserted into a major vein or artery, usually in the neck or groin area, and guided into the chambers of the heart by appropriate manipulation through the vein or artery. Such catheters must facilitate manipulation of the distal tip or ablation segment so that the distal electrode(s) can be positioned against the tissue region to be ablated. The catheter must have a great deal of flexibility to follow the pathway of the major blood vessels into the heart, and the catheter must permit user manipulation of the distal ablation segment even when the catheter is in a curved and twisted configuration. Because of the high degree of precision required for proper positioning of the tip electrode, the catheter must allow manipulation with a high degree of sensitivity and controllability.

An important factor which has driven the recent development of curative catheter ablation therapies for atrial fibrillation has been the development of a successful surgical procedure, the "Maze" procedure, for treating patients with this arrhythmia. The Maze procedure was developed to provide both sinus node control of ventricular rate and effective, appropriately synchronized biatrial contraction. This procedure involves opening the patient's chest cavity with a gross thoracotomy, usually in the form of a median sternotomy, to gain access into the patient's thoracic cavity, and cutting long linear incisions through the heart wall to electrically partition portions of the heart. In particular, the Maze procedure partitions the atria such that: (1) no portion of the atrium is large enough to support atrial fibrillation; (2) conduction of the sinus impulse to the AV node and to most portions of the atria is maintained; and (3) relatively normal atrial contraction is restored.

The success of the Maze procedure has driven interest in the development of a catheter ablation procedure which can replicate the therapeutic results of the surgical Maze procedure. This catheter ablation procedure involves the creation of relatively long linear lesions along the heart tissue with the distal tip of an ablation catheter. This desire to produce linear lesions has led to catheter designs in which several ablation electrodes are mounted on the length of the distal ablation segment of the catheter shaft. By engaging the entire length of the distal ablation segment with the heart tissue, a string of "point" lesions are connected together to form a linear lesion. When contact of the distal ablation segment shaft is attempted with standard catheter designs, however, the line of force to the ablation segment is typically applied from the proximal end, while the distal tip of the ablation segment remains relatively free. Consequently, contact pressure of the distal tip of such a catheter is dependent upon the relative stiffness of the distal ablation segment, and the translation of force by the operator through the main catheter shaft to the proximal portion of the ablation segment. This inefficient application of force along the distal ablation segment of the catheter results in non-uniform (and often inadequate) application of contact pressure at each point along the distal ablation segment.

SUMMARY OF THE INVENTION

The present invention provides devices and methods for applying electrical energy to a patient. In particular, the invention provides a steerable electrophysiology catheter for mapping and/or ablation of heart tissue during procedures such as atrial and ventricular tachycardias, particularly atrial fibrillation and flutter. The catheter of the present invention applies a centralized force to a distal ablation segment, which more uniformly distributes across the distal ablation segment to establish continuous contact pressure between the ablation segment and the patient's heart tissue. This uniform continuous contact pressure allows the operator to engage substantially the entire length of the distal ablation segment against the heart tissue to provide a relatively long, linear lesion on this tissue.

A steerable electrophysiology catheter according to the invention includes a shaft having distal and proximal ends and an ablation segment at the distal end. One or more electrodes are spaced along the ablation segment, and coupled to a source of energy by a connector extending through the shaft. Energy sources may include direct current electrical energy, radiofrequency electrical energy, microwave energy laser energy, cryoenergy, ultrasound and the like. Preferably, the energy source is a radiofrequency generator. The distal ablation segment is movable between a collapsed configuration sized for percutaneous, intercostal and/or endoluminal delivery to the target site, and an expanded configuration, in which the distal ablation segment forms a substantially continuous surface transverse to the shaft axis for engaging the heart tissue and forming a continuous lesion thereon. The catheter includes one or more force element(s) positioned to apply an axially directed force between opposite ends of the ablation segment. The force element(s) provide a centralized and substantially uniform axial force against the ablation segment to increase the contact pressure between the electrodes spaced along the ablation segment and the heart tissue. This increased contact pressure allows engagement of substantially the entire ablation segment against the heart tissue so that a continuous linear lesion may be formed on the tissue.

Another advantage of the present invention is that the distal ablation segment is preferably coupled to the catheter shaft by a substantially rigid hinge assembly. The hinge assembly allows the distal ablation segment to pivot about the shaft into a suitable orientation transverse (i.e., angles from about 1–359 degrees relative to the shaft axis) to the shaft axis for creating a linear lesion on the tissue. The rigid hinge assembly effectively secures the ablation segment in this transverse orientation so that the surgeon can apply pressure against the ablation segment (either distal or proximally directed forces) to maintain contact pressure between substantially the entire length of the segment and the heart tissue.

In one embodiment, the distal ablation segment has a split-tip configuration comprising first and second arm segments pivotally coupled to a hinge assembly at the distal end of the catheter shaft. The arms are pivotable about the hinge assembly between a collapsed configuration, where the arm segments are folded together and generally parallel to the shaft axis, and an expanded configuration, where the arms are split apart to form a continuous surface transverse to the shaft axis. Usually, the arms will define an angle between about 1 to 270 degrees in the expanded position, preferably about 90 to 180 degrees and more preferably between about 120 to 175 degrees. This latter configuration causes a spring-like contact at the ends of the ablation arms to facilitate the application of axial force by the catheter shaft against the arms. Each arm segment includes a plurality of ablation electrodes formed on an outer surface of the arm segments. Electrical connectors extend from the electrodes, through the hinge assembly and the catheter shaft, to a proximal connector for coupling the electrodes to a source of electrical energy, such as a Radiofrequency generator, or other suitable energy source.

In one aspect of the invention, the arm segments are substantially cylindrical, and the electrodes are coils, rings, half-rings or balloons extending around the cylindrical arms. In another aspect of the invention, the arm segments have a semi-circular cross-section with a substantially planar contact surface. Flattened coil electrodes or metallic pads attached to underlying support plates or other suitable electrodes are disposed on the planar contact surface. In this latter arrangement, the hinge assembly includes a pair of hinges that are offset from the shaft axis and disposed adjacent each other to minimize interference with the tissue/electrode interface.

In yet another aspect of the invention, each arm segment also includes a fluid channel for directing coolant therethrough to bathe the target site with fluid and/or convectively cool the electrodes. In an exemplary embodiment, the fluid is an ionic solution, such as isotonic saline. In this configuration, the fluid is directed between the electrodes and tissue at the target site to complete the current path between the electrodes and the tissue. The ionic solution effectively carries the RF ablation energy to inhibit or prevent direct contact between the electrodes and the tissue to minimize tissue damage and fluid (e.g., blood) coagulation on the electrodes.

The force element(s) are preferably disposed between the arm segments at the hinge assembly, and include a connector extending to the proximal end of the catheter shaft. Preferably, at least one of the force elements is the catheter shaft, which can be manipulated to apply a central, symmetric axial force against the arms at the hinge assembly in the expanded position to effectively ensure that the arms maintain sufficient contact pressure against the heart tissue during the ablation procedure. The force element(s) may also actuate the hinge assembly to pivot the arm segments between the folded and expanded positions. In a specification configuration, the force element(s) additionally include one or more actuator wires extending through the catheter shaft from a proximal handle to the hinge assembly. The handle includes a user input control, such as a slide ring, knob, button or the like, for axially translating the manipulator wires. This axial translation of the actuator wires causes the arm segments to pivot about the hinge assembly. The handle may include additional input controls for providing additional degrees of freedom, such as rotation of the ablation segment about the catheter shaft, curvature of the catheter tip, and the like.

In another embodiment of the invention, the distal ablation segment includes a single, linear ablation segment coupled to the catheter shaft by a pair of curved, flexible support shafts. The curved support shafts extend radially and distally outward from the catheter shaft to support the linear ablation segment at points between its ends and midspan. The ablation segment includes a central hinge structure and outer movable portions that pivot about the hinge structure. A centrally mounted pull wire within the catheter shaft causes the outer portions of the ablation segment to collapse and expand at the central hinge pivot point. The outer portions of the ablation segment preferably define an angle of about 120 to 170 degrees in the expanded configuration. The support shafts, together with a central manipulator wire, function as the force elements to apply a balanced axial force against the ablation segment in the expanded configuration. Alternatively, the catheter shaft may include a pair of flexible arms that extend distally away from each other to form a Y-shaped arrangement at the distal end of the shaft. In this configuration, the arms are biased toward each other, and can be pivoted about a central "living" hinge to urge the arms into an expanded configuration.

In another embodiment of the invention, the distal ablation segment is a single, continuous member that pivots around the distal end of the catheter (rather than collapsing upon itself as in the previous embodiments). The distal portion of the catheter shaft preferably includes a cut-out or longitudinal opening for allowing the ablation segment to pivot from a collapsed or generally parallel orientation within the longitudinal opening of the shaft to a deployed orientation transverse to the shaft. The ablation segment may also be drawn proximal into the shaft, if desired. The force elements in this embodiment preferably include the catheter shaft and a pair of curved flexible support shafts that extend from the distal end of the catheter shaft to support the ablation segment. One of the support shafts may also be drawn proximally into the catheter to pivot the ablation segment about the distal end of the catheter.

In a preferred aspect of a method of the present invention, an ablation segment is positioned adjacent the target site on the patient's heart. The ablation segment may be introduced and delivered endoluminally to the target site with a delivery catheter, it may be delivered through an intercostal penetration with a catheter or probe, or directly into the thoracic cavity through a thoracotomy. Once in position, the pull wire(s) are moved axially to pivot the arm segments (or rotate the single ablation segment) into the expanded position transverse to the shaft axis. The catheter can then be moved distally to engage the heart tissue at the target site. The actuator wires, catheter shaft and/or support shafts will exert an axial force against the distal ablation segment to maintain sufficient contact pressure with the heart tissue so that the electrodes create a linear lesion against this tissue. In an exemplary embodiment, the surgeon will create a number of linear lesions in the heart tissue to electrically partition portions of the atria (i.e, similar to the Maze procedure).

Alternatively, if the electrodes were mounted circumferentially around the arm segments, or on the "backside" of the arm segments, the catheter could be pulled proximally to engage the heart tissue. For example, the catheter may be pulled into a vessel to engage the heart tissue surrounding the vessel opening, such as the ostium of a vein or artery or a valve annulus, or against the septal wall of the left atrium through a transseptal puncture. Radiofrequency current could then be delivered through a connector in the shaft and suitable electrode wires to the electrodes on the ablation segment(s), through which current is conducted to the heart tissue to perform ablation.

Other features and advantages of the invention will appear from the following description in which the preferred embodiment has been set forth in detail in conjunction with the accompanying drawings.

BRIEF DESCRIPTION OF THE DRAWINGS

FIGS. 2A and 2B are side cross-sectional views of distal and proximal portions, respectively, of a deflectable tip of the catheter of FIG. 1;

FIGS. 2C–2E are transverse cross-sectional views taken along lines C—C, D—D, and E—E respectively, through the distal portion of the deflectable tip of FIG. 2A;

FIGS. 2F—2H are transverse cross-sectional views taken along line F—F, G—G and H—H respectively, through the proximal portion of the deflectable tip of FIG. 2B;

FIG. 3 is an enlarged view of a hinge assembly at the distal end of the catheter of FIG. 1, illustrating a split-tip configuration with a pair of cylindrical ablation segments;

FIGS. 14A and 14B illustrate the central hinge embodiment of FIGS. 13A–13C in the collapsed configuration;

DESCRIPTION OF THE SPECIFIC EMBODIMENTS

Figure 1:
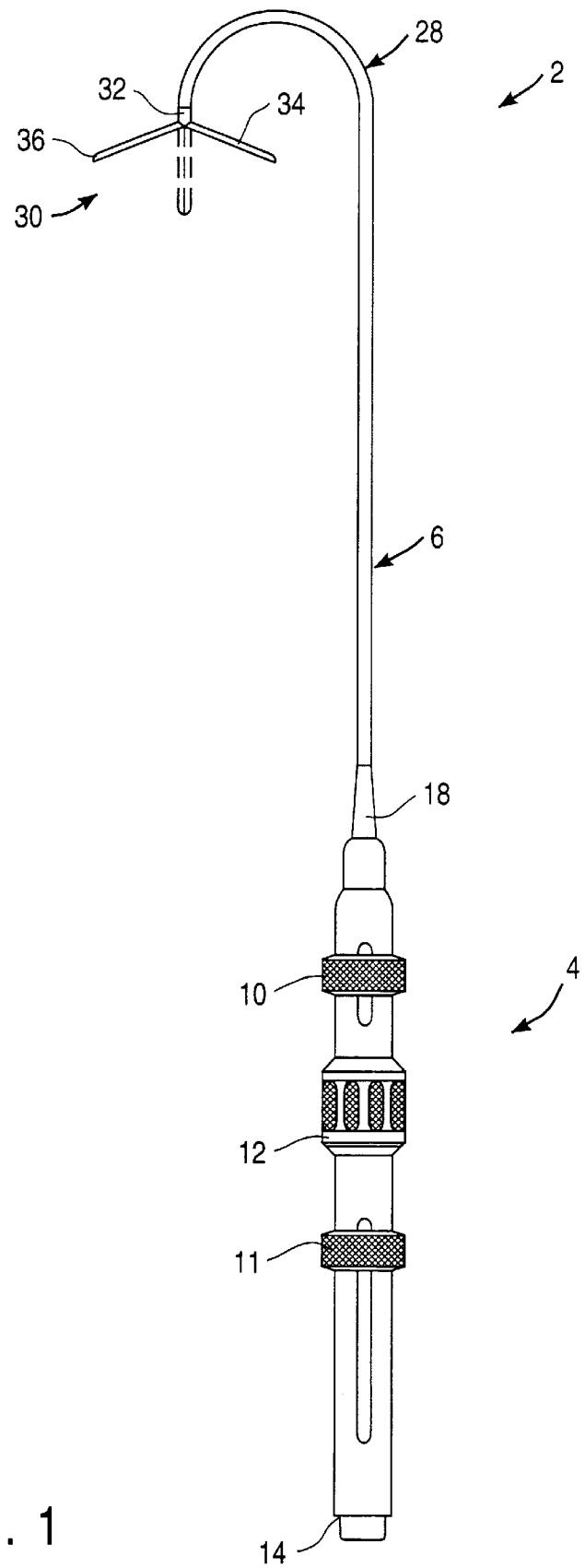
FIG. 1 is a perspective view of a steerable electrophysiology catheter constructed in accordance with the principles of the present invention.

Referring to the drawings in detail, wherein like numerals indicate like elements, an electrophysiology catheter 2 is illustrated according to the present invention. As shown in FIG. 1, catheter 2 generally includes a shaft 6 having a proximal end 18 and a distal end 22. Catheter 2 includes a handle 4 secured to proximal end 18 of shaft, and a deflectable tip 28 coupled to distal end 22 of shaft 6. Deflectable tip 28 comprises a movable ablation assembly 30 at its distal end that generally includes a hinge assembly 32 and a pair of arms 34, 36 that are movable between open (FIG. 3) and closed positions (FIG. 1). A plurality of ablation or mapping electrodes 38 (see FIGS. 3–5) are mounted to arms 34, 36 for applying electrical energy to the patient, as discussed in further detail below. Handle 4 includes a tip actuation slide 10, a core wire torque ring 12 and a curvature adjustment slide 11, as well as an electrical connector 14, all described more fully below.

FIGS. 2A and 2C–2E illustrate a distal portion 31 of deflectable tip 28, and FIGS. 2B and 2F–2H illustrate a proximal portion 33 of tip 28. It should be understood that the deflectable tip 28 illustrated in FIGS. 2A–2H represents an exemplary embodiment, and the present invention is not limited to this configuration. That is, the ablation assemblies described below may be used with a wide variety of different tips and catheters. As shown in FIGS. 2B and 2H, shaft 6 includes an axial lumen 48 between its proximal and distal ends 18, 22. The preferred construction of shaft 6 includes a polyimide or ULTEM™ inner tube 50 surrounded by an extruded topcoat 52 of a flexible polymer such as PEBAX™, urethane, etc. To add torsional and bending stiffness to shaft 6, a braided reinforcement 54, usually stainless steel, may be embedded in topcoat 52. As shown in FIG. 2H, inner tube 50 includes a number of manipulator and actuator wires, fluid channels, electrical conductors and the like, extending from its proximal end to deflectable tip 28. Deflectable tip 28, in turn, defines at least five axial lumens extending from its proximal end to its distal end, all in communication with axial lumen 48 of inner tube 50.

In one embodiment, a stiffener or manipulator wire 66 for selectively adjusting the curvature of deflectable tip 28 extends through shaft 6 into tip 28 to a distal ball 67, which is mounted to an anchor member 69 near the distal end of tip 28 (see FIGS. 2A and 2D, discussed in further detail below). As shown in FIG. 2D, manipulator wire 66 extends through a first axial lumen 55 in tip 28. When the catheter 2 has been positioned in the heart, the configuration of the deflectable tip 28 can be selectively adjusted to impart the desired curvature and shape to the deflectable tip as appropriate for the size and location of the area to be mapped and/or ablated. In one embodiment, manipulator wire 66, when advanced into tip 28, will give tip 28 and manipulator wire 66 a combined bending stiffness greater than that of deflectable tip 28 alone, but less than the bending stiffness of shaft 6. A more complete description of this feature can be found in commonly assigned U.S. Pat. No. 5,487,757, the complete disclosure of which is incorporated herein by reference.

As shown in FIGS. 2C–2G, second and third axial lumens 56, 57 within tip 28 receive actuator wires 58, 59 for manipulating arms 34, 36 of ablation assembly 30 (see FIG. 3). Actuator wires 58, 59 extend to a yoke 78 of ablation assembly 30 for manipulating the arms 34, 36, as discussed in detail below. As shown in FIG. 2H, actuator wires 58, 59 are joined into a single, common actuation member 61 within shaft 6 for actuation of both wires 58, 59 (and both ablation arms) substantially simultaneously. Of course, it will be recognized that the actuator wires 58, 59 may remain separate through shaft 6 for independent actuation of the ablation segments. Deflectable tip 28 further includes a fourth axial lumen 70 through which a core wire 72 extends. As shown in FIG. 2D, core wire 72 forms a loop in anchor member 69 at or near distal end of tip 28 to enable rotational manipulation of tip 28. In a preferred embodiment, core wire 72 extends through shaft 6 and comprises TEFLON®-coated stainless steel. Catheters utilizing such a core wire construction are disclosed in co-pending application Ser. No. 07/866,383, the complete disclosure of which has previously been incorporated herein by reference.

Referring again to FIGS. 2G and 2H, tip 28 further includes a fifth, central lumen 73 for receiving electrode wires 74, thermocouple wires 76 (see FIG. 2H)) and a fluid tube 75. Of course, each of these components may extend through separate lumens, rather than one, larger central lumen 73. As shown in FIG. 2F, fluid tube 75 is preferably coupled to a pair of fluid conduits 85, 87 extending through tip 28 to the ablation segments for delivering fluid to each segment as discussed below. In an exemplary embodiment, fluid conduits 85, 87 are bonded to fluid tube 75 with a fluid tight sheath 89 formed of a suitable material, such as a Dacron™ mesh impregnated with a silicone adhesive. Each of electrode wires 74 is connected to one of the electrodes 38 (FIG. 3). In the representative embodiment, wires 74 are bundled together through shaft 6 (see FIG. 2H) and then split apart into two flex circuits 77, 79 (FIG. 2F), each extending to one of the ablation segments, as discussed below. As shown in FIG. 2G, flex circuits 77, 79 are joined to wires 74 at a junction 81 within tip 28 having an insulating adhesive dome 83. The thermocouple wires 76, typically copper and constantan, extend into an aperture (not shown) in arms 34, 36, where they are anchored with high temperature adhesive.

Referring again to FIGS. 2A, 2C and 2D, yoke 78 includes an annular mounting portion 91 extending into tip 28, where it is attached to anchor member 69. Anchor member 69 is a substantially annular member that is coupled to the outer walls of tip 28 (see FIG. 2A). As shown in FIG. 2D, anchor member 69 has a pair of cut-outs 93, 95 for receiving actuation wires 58, 59 and a number of holes for receiving manipulator wire 66, central lumen 73 and core wire 72. Core wire 72 loops around the distal end of anchor member 69 to form the core wire loop, thereby anchoring core wire 72 to tip 28. Accordingly, anchor member 69 includes two holes 97 for receiving both portions of the core wire 72 loop.

Referring to FIGS. 3–5 and 12, one embodiment of the ablation assembly 30 of the present invention will be described in further detail. As shown in FIG. 3, ablation assembly 30 includes a hinge assembly 32 coupled to the distal end of deflectable tip 28, and a pair of shaft segments or arms 34, 36 pivotally mounted to hinge assembly 32. Specifically, hinge assembly 32 includes a yoke 78, a pair of hinges 80, 82 mechanically linked to yoke 78 and a pair of actuator wires 58, 59 coupled to hinges 80, 82. Hinges 80, 82 preferably comprise a relatively strong metal, such as titanium, stainless steel, Nitinol™ or engineering plastics, such as Ultem™. Actuator wires 58, 59 extend through the catheter shaft to tip actuation slide 10 (FIG. 1) of handle 4 for mechanically opening and closing arms 34, 36 (discussed below). Arms 34, 36 will usually be configured to move between a closed position (dotted lines in FIG. 1) substantially parallel to the longitudinal axis of shaft 6 and an open position having an included angle of about 1 to 270 degrees in the expanded position, preferably about 90 to 180 degrees and more preferably between about 120 to 175 degrees. This latter configuration causes a spring-like contact at the ends of the ablation arms to facilitate the application of axial force by the catheter shaft against the arms. The actual application of arms 34, 36 to the irregularities of the surface of the interior of the heart will probably be most extensive (and effective) with an included angle of less than 150 degrees.

Once arms 34, 36 have been expanded and positioned in engagement with the heart tissue, catheter shaft 6, 28 will be used to apply an axial force against arms 34, 36 to maintain continuous contact pressure against the tissue. As those skilled in the art will appreciate, catheter shaft 6, 28 can be manipulated to apply a centralized, symmetric and evenly balanced axial force against arms 34, 36, which allows a relatively long area of tissue to be engaged by two shorter segments (i.e., arms 34, 36). In addition, the arms 34, 36 provide increased and evenly distributed contact pressure across the entire length of the desired ablation location. Actuator wires 58, 59 close arms 34, 36 against the tissue, which enhances the contact therebetween. In the preferred embodiment, proximal movement of actuator wires 58, 59 (i.e., pulling on these wires) will close arms 34, 36, while distal movement or pushing on wires 58, 59 will open arms 34, 36. However, it will be recognized that arms 34, 36 may be actuated in the reverse direction.

Referring to FIG. 3, each arm 34, 36 will include a plurality of ablation electrodes 38 extending along the length of arms 34, 36 (note that electrodes 38 are only schematically illustrated in the drawings). Preferably, ablation electrodes 38 are coils or solid rings that are spaced from each other along arms 34, 36 and include temperature sensors 88, such as thermocouples or thermistors. The electrodes 38 and temperature sensors 88 are electrically coupled to wires 74, 76 within shaft 6 by individual insulated wires 90, 92, respectively (see FIG. 12). However, they may also be electrically connected by flexible conductors (not shown), such as flex circuits, silicon matrix multi-filar ribbon cables, or the like. Flexible conductors have the advantage that they will be more reliable during repeated flexion at the hinge points. Arm segments 34, 36 will be constructed to have a desirable stiffness, depending on the application. For example, relatively stiff arm segments 34, 36 could be useful in flatter areas of the atrium, while a softer construction would be more conformable to curved (particularly convex) portions of the atrium. Softer arm constructions could be made to conform around a sharp bend in the contact surface, such as the ostium of a vein or artery or a valve annulus. The length of arm segments 34, 36 will also vary depending upon the number of electrodes 38 desired. Typically, each arm will include one to three electrodes 38, which results in an arm length of about 1–3 cm or an overall ablation length of 2–6 cm. However, it will be readily recognizable that the arms may be longer or shorter depending on the particular procedure.

Figure 4:
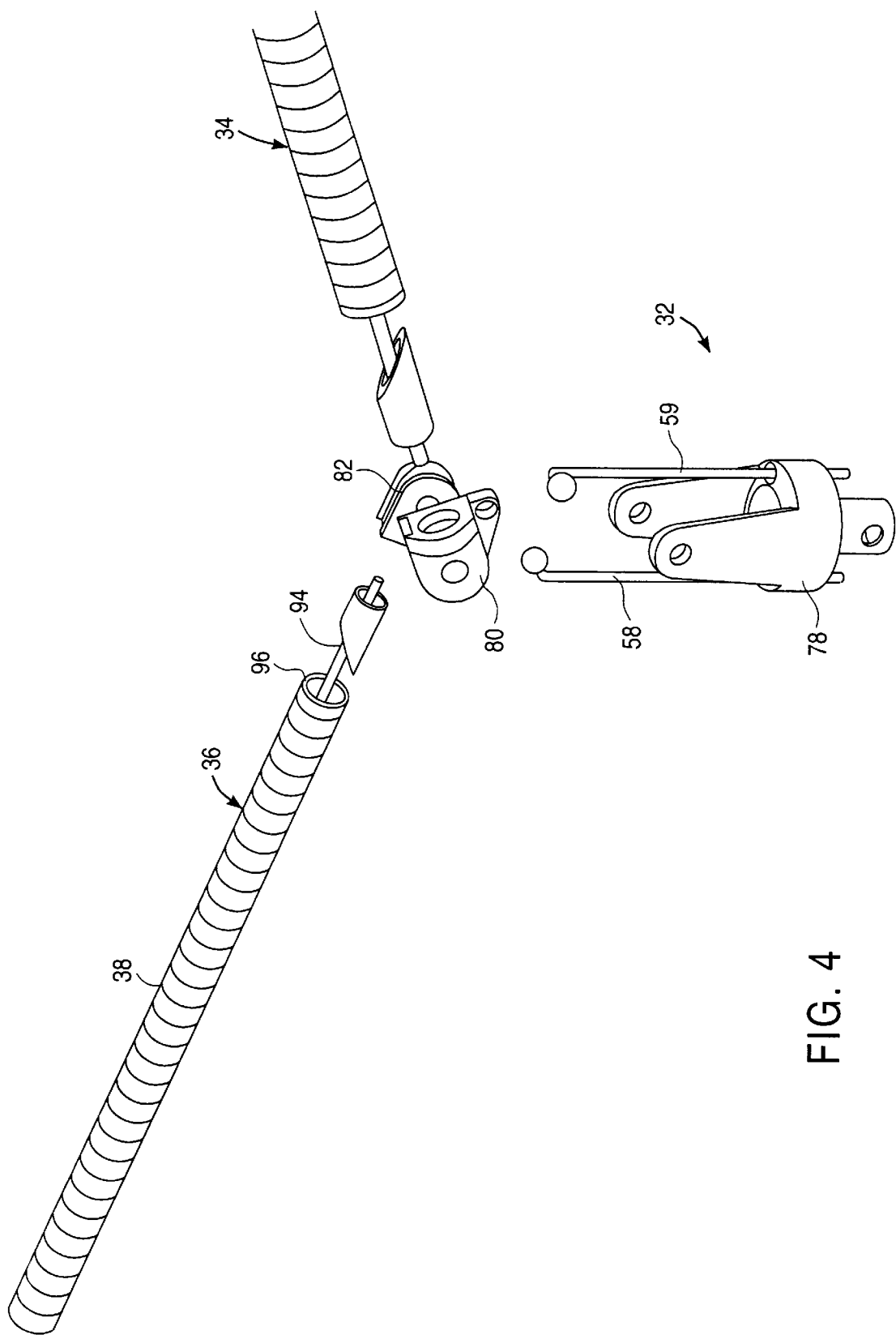
FIG. 4 is an exploded view of the hinge assembly of FIG. 3.
Figure 5:
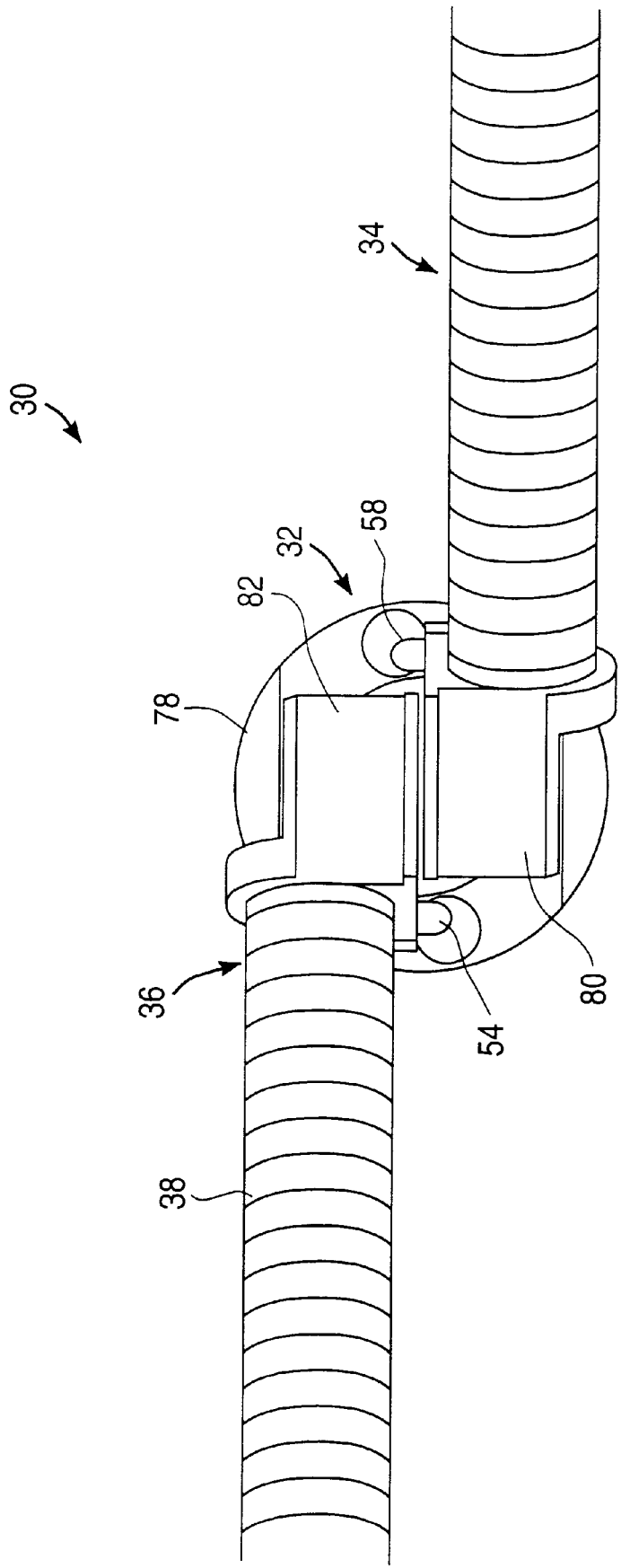
FIG. 5 is an end view of the hinge assembly of FIG. 3.
Figure 12:
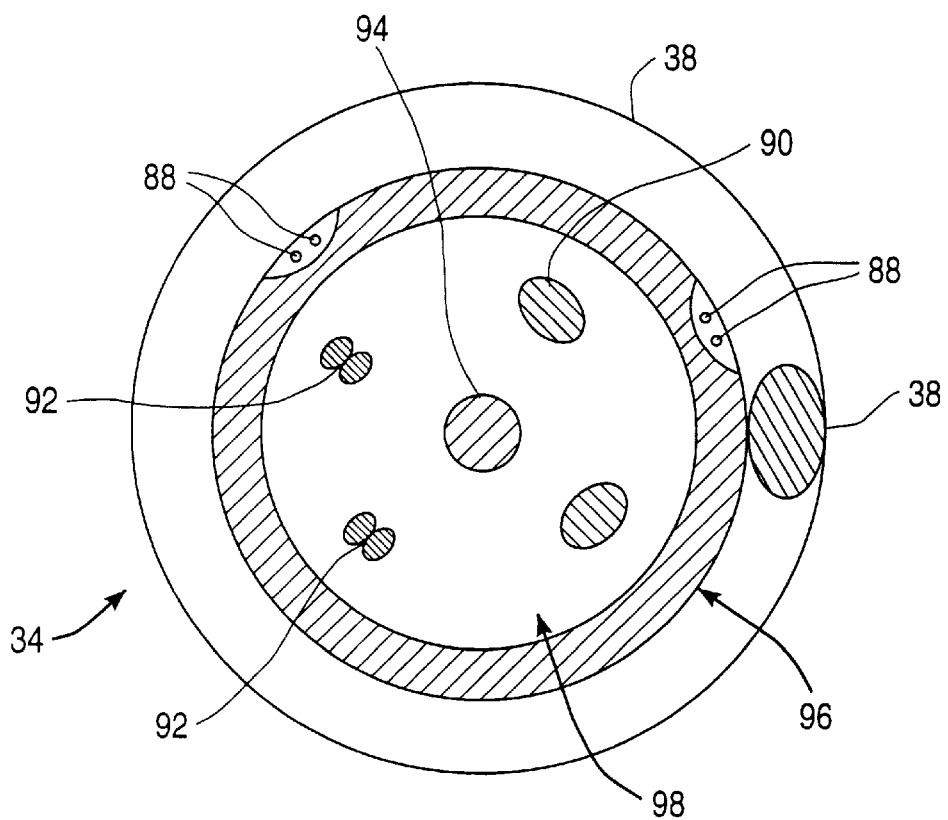
FIG. 12 is a cross-sectional view of one of the ablation segments of the hinge assembly of FIG. 3.

As shown in FIGS. 4 and 12, arm segments 34, 36 may have a circular cross-section, comprising a central mandrel core 94 attached, e.g., glue, solder, weld, press-fit, or the like, at hinges 80, 82, and outer sleeves 96 extending coaxially over mandrel cores 94. Core 94 and outer sleeves 96 define an annular fluid passage 98 therebetween, which is fluidly coupled to a fluid lumen (not shown) within catheter shaft 6. Arms 34, 36 may include a plurality of holes along their length for directing coolant onto the target site. Alternatively, arms 34, 36 may each include a hole at their distal ends for allowing the coolant to flow through arms to convectively exchange heat with electrodes 38. A more complete description of this method of cooling electrodes 38 can be found in commonly assigned, co-pending application "Fluid Cooled Ablation Catheter and Method for Making" U.S. Pat. No. 5,913,854 (attorney docket no. 14875-003400), Serial No. unassigned, filed concurrently with the present application, the complete disclosure of which has previously been incorporated herein by reference.

As shown in FIGS. 2–5, the curvature imparted to deflectable tip 28 may be selectively adjusted by axially translating manipulator wire 66 within the catheter shaft 6. Preferably, the curve control allows orientation of deflectable tip 28 between 0–270° of curve, more preferably between 0–180°. Catheter 2 may include another control wire (not shown) extending to yoke 78 for rotating ablation assembly 30 by twisting deflectable tip 28 relative to shaft 6. Typically, this control wire is a tapered core wire which can be rotated to cause slight twisting of the main catheter shaft 6, thereby allowing the angular orientation of the open hinge arms 34, 36 to be varied relative to shaft 6. This allows the operator to rotate the position of arms 34, 36 without physically rotating the entire catheter shaft 6, which provides for finer control of this manipulation. When the distal shaft is curved, rotation of the tapered core wire causes lateral movement of the entire distal array.

In a method according to the present invention, catheter 2 is transluminally, thoracoscopically (e.g., through an intercostal penetration), and/or directly delivered into the thoracic cavity so that deflectable tip 28 is positioned adjacent the heart. An axial force may be applied to manipulator wire 66 by sliding adjustment slide 11 to adjust the curvature of tip 28. When the desired degree of curvature has been obtained, deflectable tip 28 may be further positioned rotationally by rotating torque ring 42, thereby exerting torque on core wire 42 or an additional control wire (not shown) which rotates the deflectable tip about the longitudinal axis. When ablation assembly 30 has been positioned near a desired target site, actuator wires 58, 59 are moved distally to pivot arms 34, 36 about hinges 80, 82, preferably until arms 34, 36 are positioned transverse to the shaft axis. Catheter 2 can then be moved distally (or proximally) to engage the heart tissue at the target site with arms 34, 36. Catheter shaft 6 will exert an axial force against arms 34, 36, and tensioning or pulling of wires 58, 59 will enhance the contact of arms 34, 36 against the heart tissue to maintain uniform contact pressure with the tissue. Radiofrequency current is then delivered through connector 46 and electrode wires 74 to electrodes 38, through which current is conducted to the heart tissue to perform ablation. Mapping may also be accomplished when catheter 2 is used with an ECG.

Figure 15:
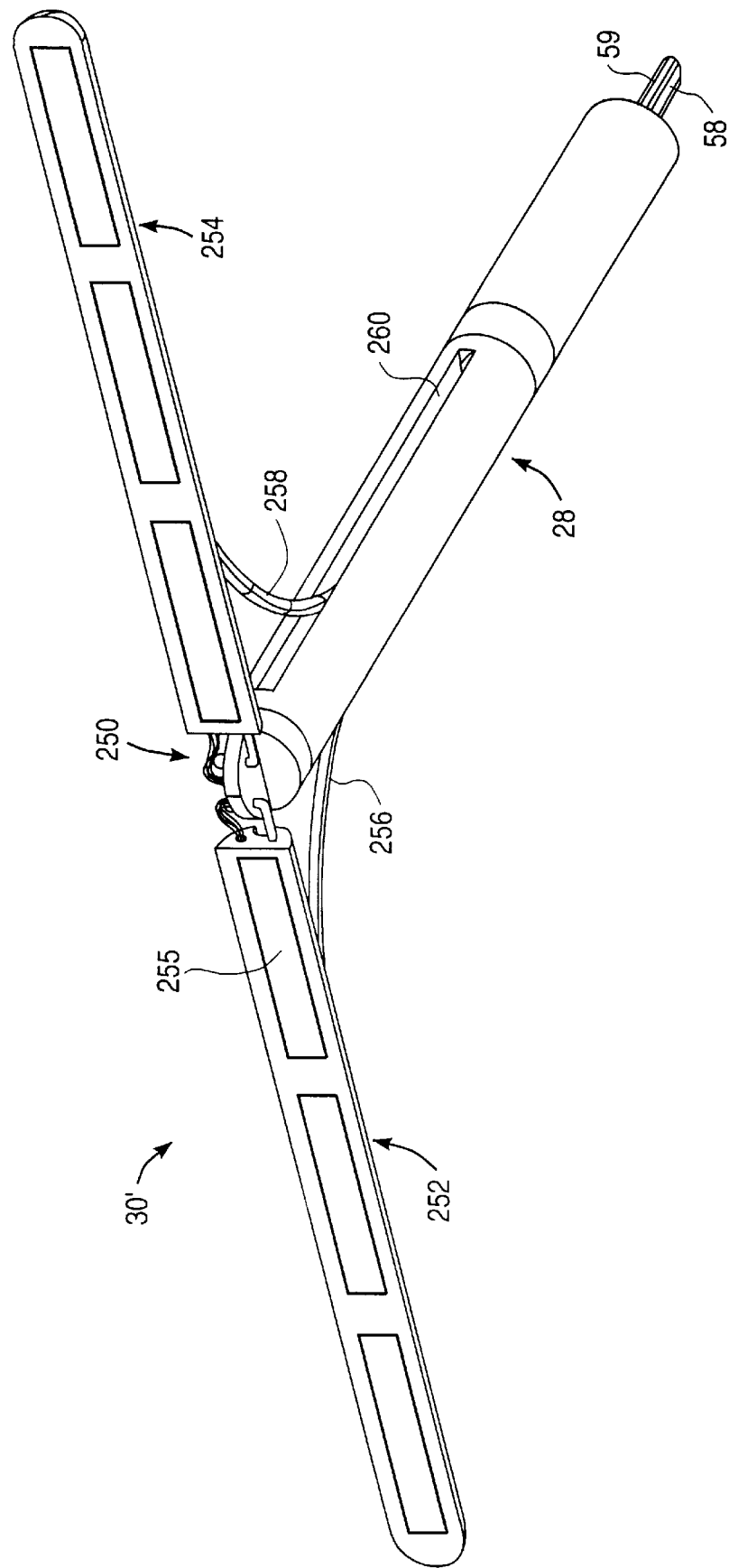
FIG. 15 illustrates yet another embodiment of the hinge assembly of the present invention.
Figure 16:
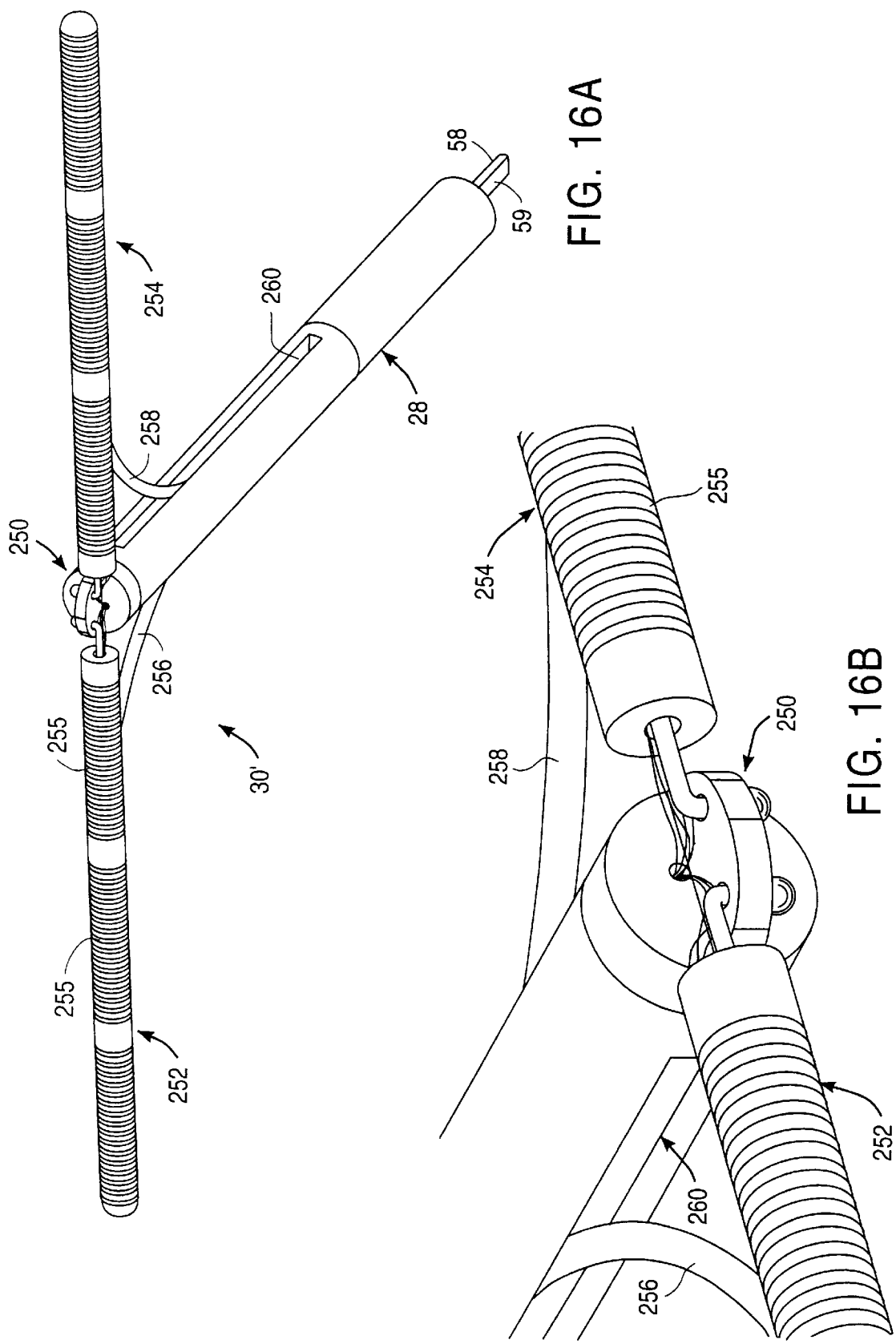
FIGS. 16A and 16B illustrate another embodiment of the hinge assembly of the present invention.

The present invention is not limited to the hinge assembly described above and shown in FIGS. 3–5. For example, an alternative ball and socket hinge design is illustrated in FIGS. 15, 16A and 16B. As shown in FIG. 15, ablation assembly 30' includes a ball and socket rotational linkage 250 pivotally coupled to a pair of arm segments 252, 254. A plurality of ablation or mapping electrodes 255 are disposed on each arm segment 252, 254 as described above. Arms segments 252, 254 may have a semi-circular cross-sectional shape (FIG. 15), or a cylindrical shape (FIGS. 16A and 16B). Each arm 252, 254 is movably coupled to deflectable tip 28 by a curved support wire or shaft 256, 258, respectively.

Support wires 256, 258 extend from arms 252, 254 into slits 260 in deflectable tip 28, where they are coupled to actuator wires 58, 59 for pivoting arms 252, 254 about linkage 250. In use, arms 252, 254 may be pivoted between a closed position (not shown) on either side of, and substantially parallel to, tip 28, and an open position (FIG. 15) transverse to tip 28. In the open position, support wires 256, 258 support arms to facilitate their engagement with the patient's tissue.

Figure 6:
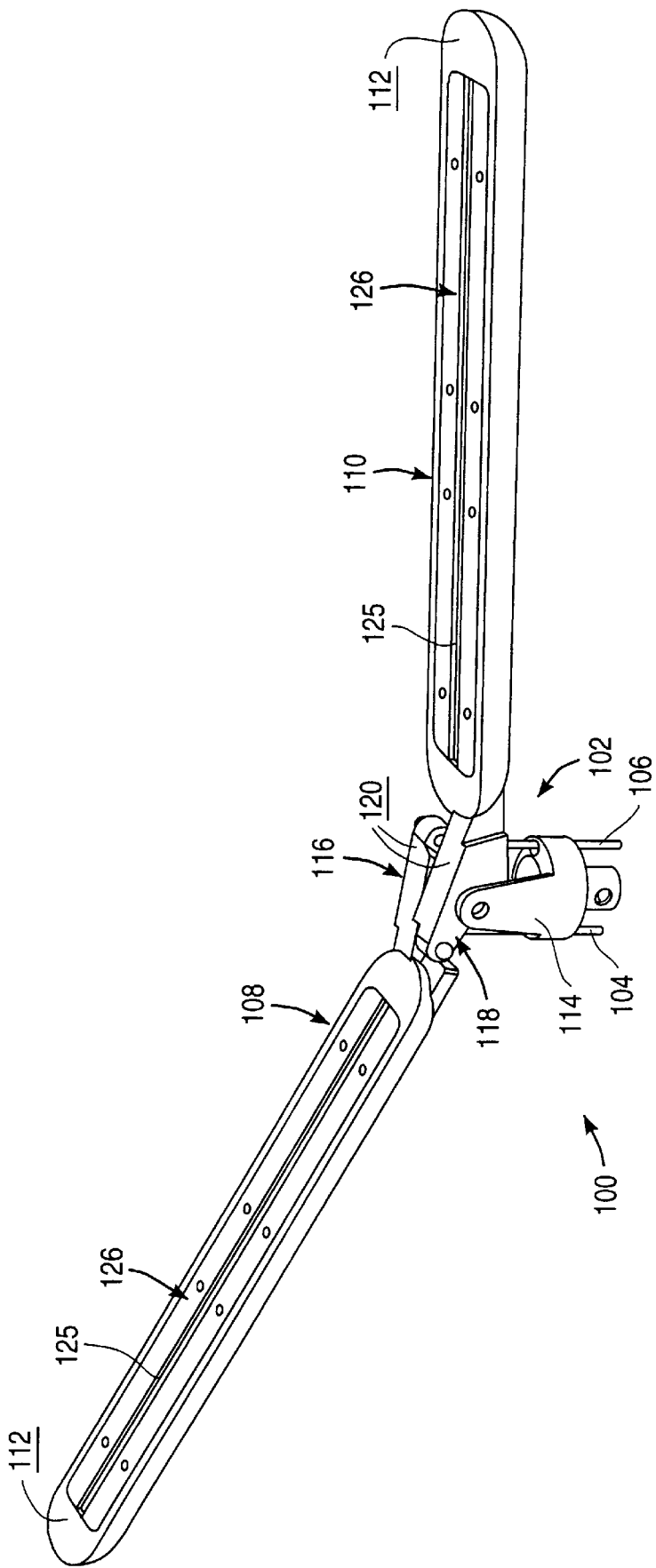
FIG. 6 is an enlarged view of an alternative hinge assembly incorporating an integrated central hinge element and semi-circular ablation segments with substantially planar electrodes thereon.
Figure 7:
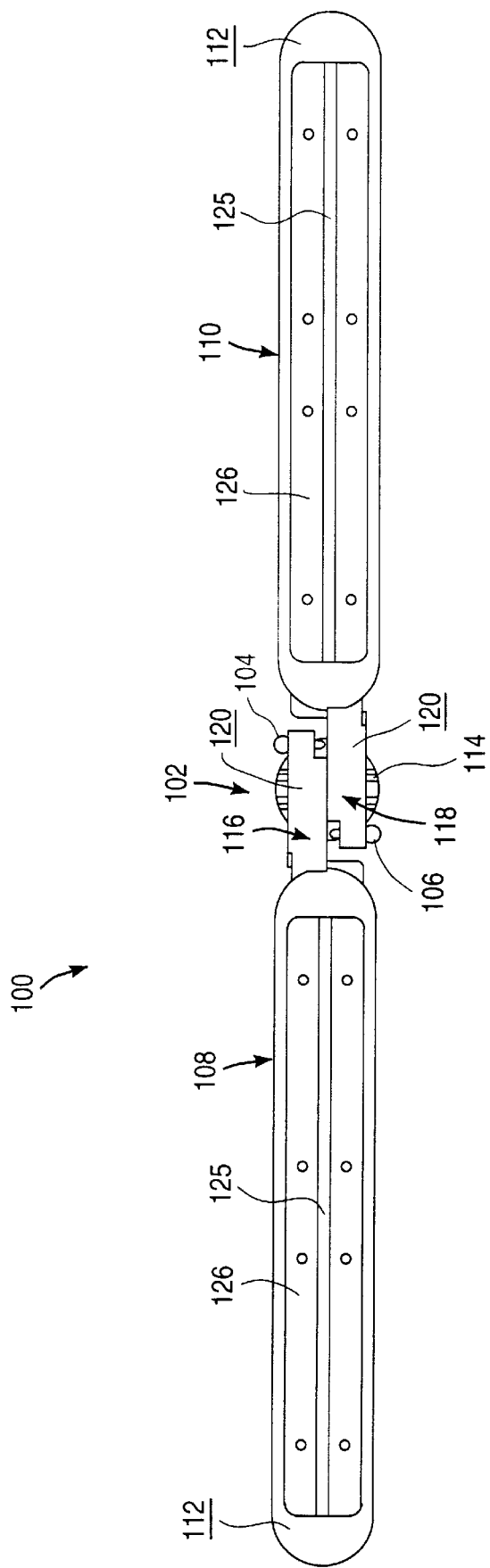
FIG. 7 is an end view of the alternative hinge assembly of FIG. 6.
Figure 8:
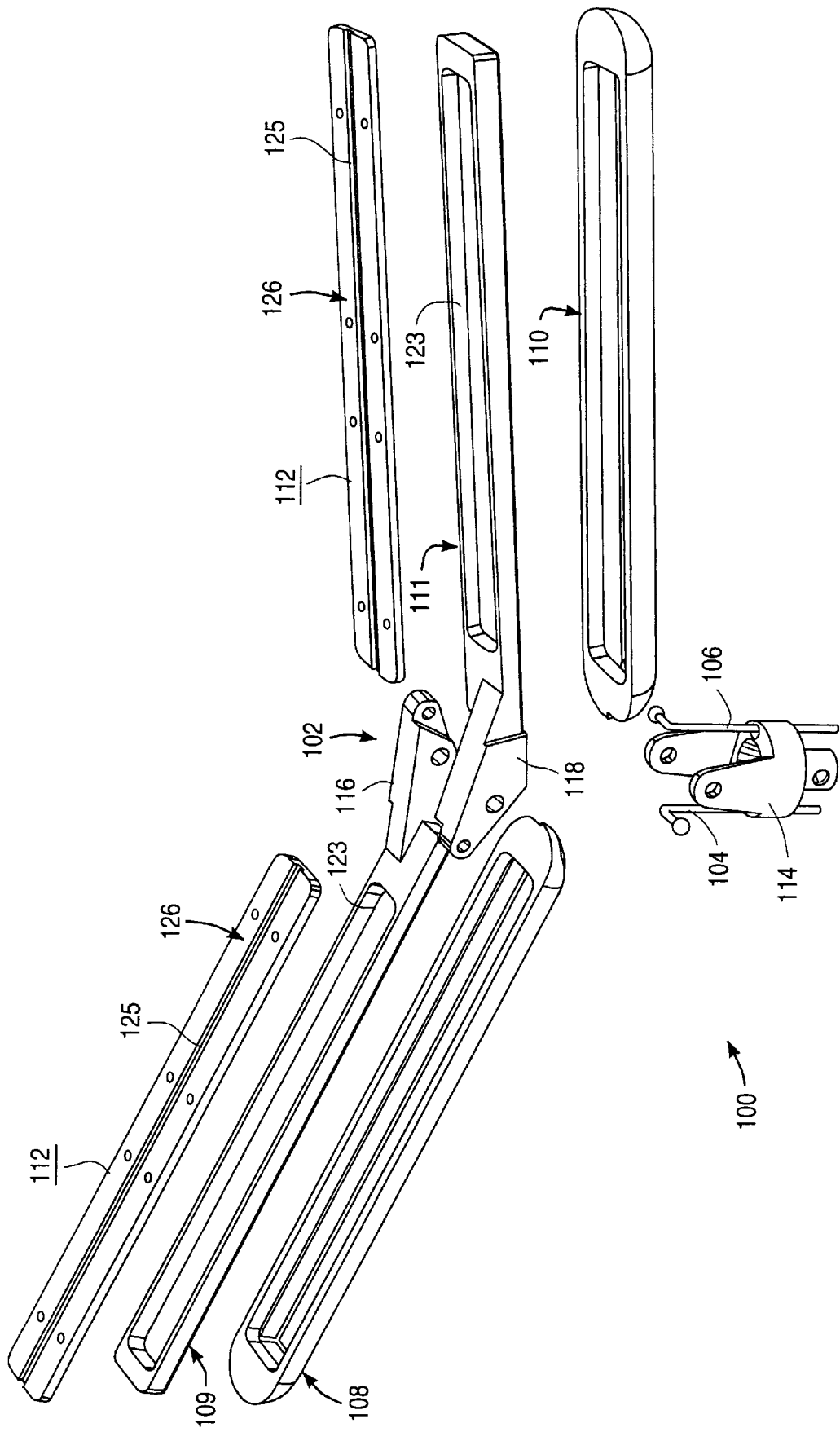
FIG. 8 is an exploded view of the hinge assembly of FIG. 6.
Figure 9:
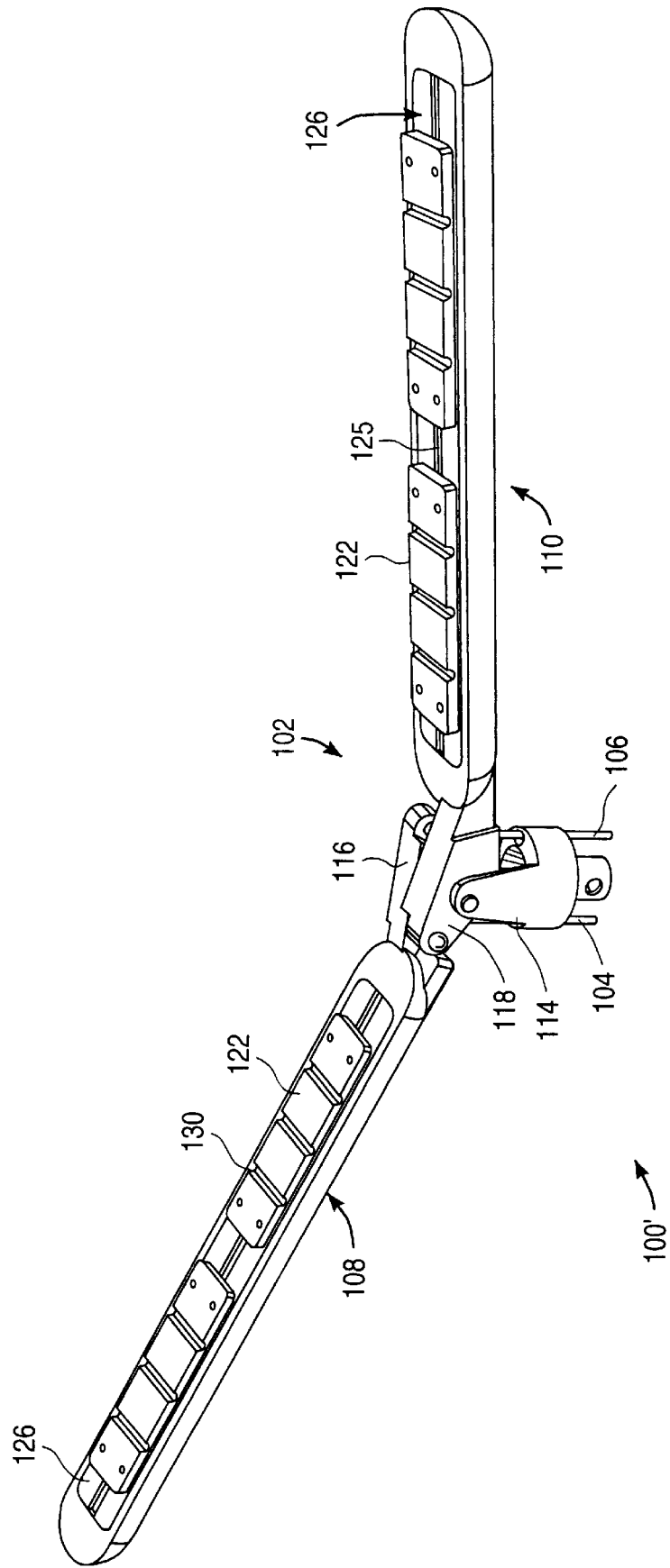
FIG. 9 is an enlarged view of the hinge assembly of FIG. 6, incorporating a plurality of metallic pad electrodes on the ablation segments.

FIGS. 6–10 illustrate another embodiment of a distal ablation assembly for use with catheter 2 according to the present invention. Similar to the previous design, ablation assembly 100 includes first and second arm segments 108, 110 pivotally coupled to a central hinge member 102. As shown in FIG. 8, central hinge member 102 includes a pair of longitudinal support members 109, 111 each having an integral hinge 116, 118. Support members 109, 111 can be designed (as shown) with a recess or plenum 123 for delivery of fluid under and to the electrodes 122 mounted on top (see FIGS. 9 and 10). Mounting/cover plates 126 cover the plenum channels 123 and provide surface for mounting electrodes 122 (as shown in FIG. 9). Cover plates 126 may have holes for passing fluid to or through the electrodes 122 mounted thereto (not shown). A central line channel 125 provides a conduit for running electrical wires and/or thermocouples to the electrodes 122. In this embodiment, arm segments 108, 110 have a semi-circular cross-sectional shape (see FIG. 11), and are preferably formed using a silicone liquid injection molding (LIM) technique to mold-form arm segments 108, 110 around support members 109, 111. As shown, ablation assembly 100 further includes a yoke 114 and a pair of actuator wires 104, 106 for pivotally coupling arms 108, 110 and support members 109, 111 to catheter shaft 6 (FIG. 1). Hinges 116, 118 are preferably offset from the yoke 114 axis so that hinges 116, 118 can be disposed adjacent each other (FIG. 6). Hinges 116, 118 are designed to minimize interference with the planar contact of cover plates 126 with the tissue (i.e., hinges 116, 118 do not protrude outward when arm segments 108, 110 are open).

Figure 10:
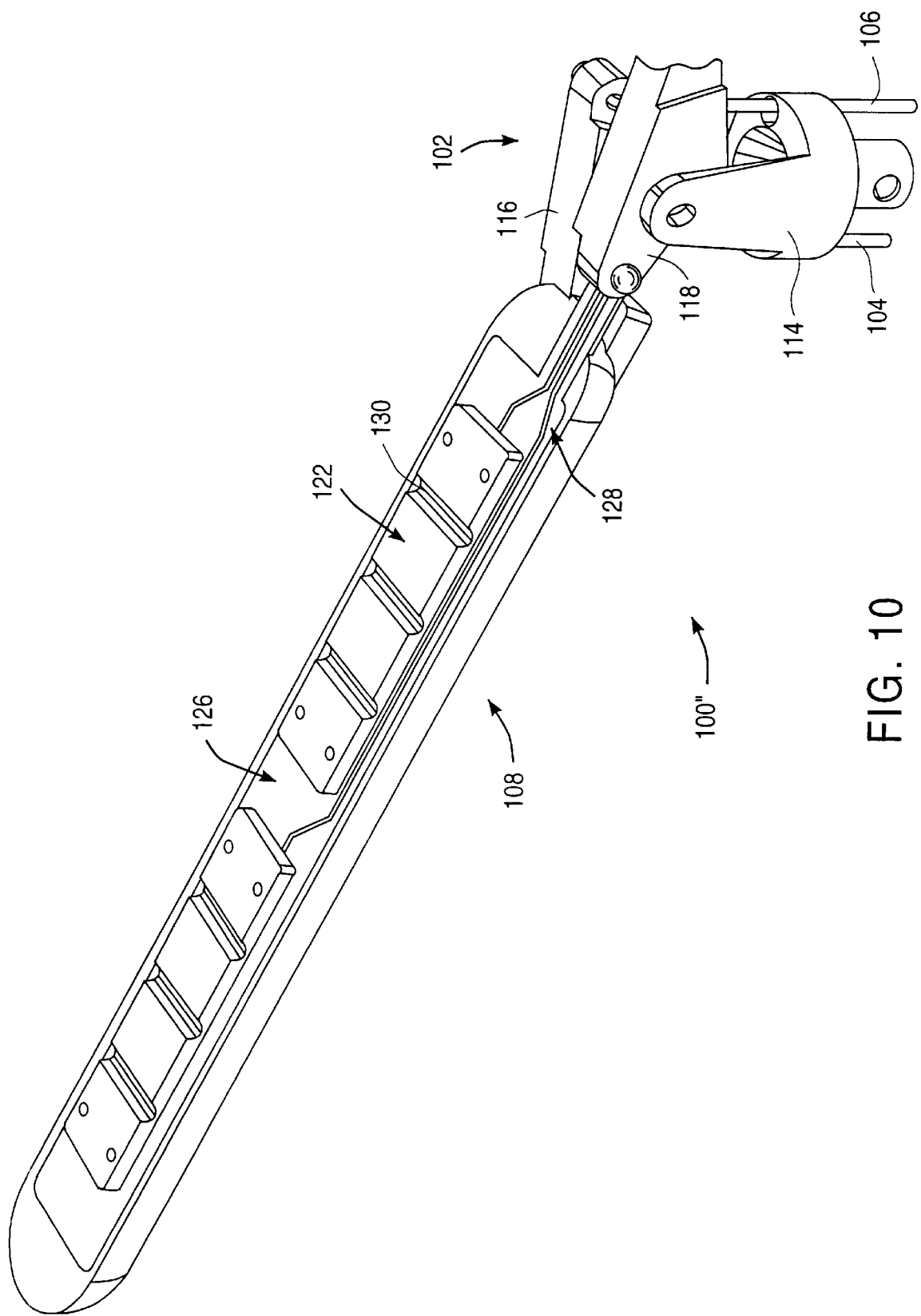
FIG. 10 is an enlarged view of one of the ablation segments of the hinge assembly of FIG. 9.

Arm segments 108, 110 each include a plurality of electrodes 122 disposed on cover plates 126. In one configuration, electrodes 122 have a flattened coil design (not shown) to provide a relatively flexible electrode length. In another configuration, electrodes 122 each comprise a metallic pad 124 mechanically or adhesively attached to cover plate 126 (FIG. 9), or in an alternative configuration, to an underlying flexible printed circuit 128 (FIG. 10). Flexible printed circuits 128 provide a reliable electrical connection from electrodes 124, around the hinge joint 102, to connection wires 74 in shaft 6 (see FIGS. 2A–2C). In addition, flexible printed circuits 128 may include a thermocouple junction (not shown) across several layers in the circuit for providing temperature sensing. As shown in FIG. 8, electrode pads 124 are preferably relatively thick (i.e., on the order of about 0.005 to 0.020 inch), and include notches 130 that provide mechanical bending points to increase flexibility of pads 124. Alternatively, electrode pads 124 may comprise a thin film on the order of about 0.0001 to 0.005 inch thick, or a flexible grid or mesh arrangement (see FIGS. 18A and 18B).

Figure 11:
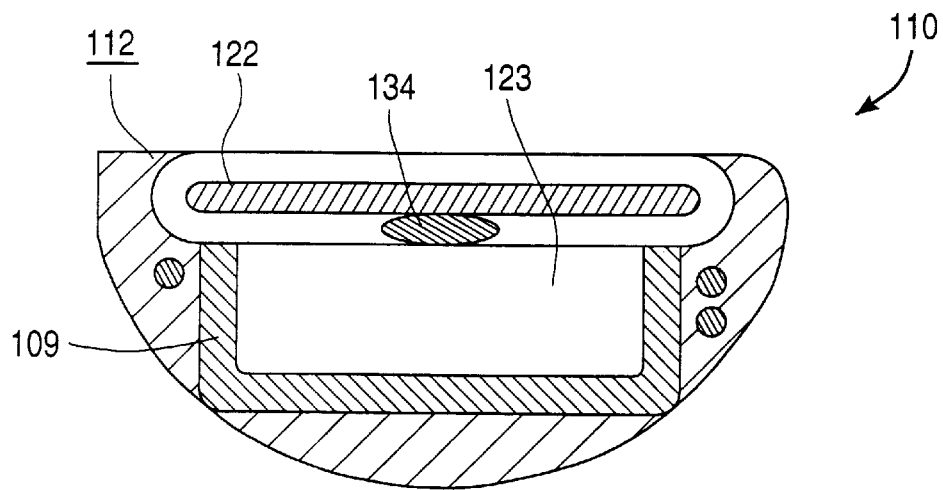
FIG. 11 is a cross-sectional view of one of the ablation segments of the hinge assembly of FIG. 6.

As shown in FIG. 11, arm segments 108, 110 each include a fluid channel through recesses 123 of support members 109, 111, which are preferably made of a suitable thermoplastic material, such as ULTEM™ or metal. The fluid channels or recesses 123 are coupled to a fluid lumen (not shown) in catheter shaft 6 for allowing fluid coolant to exchange heat with electrodes 122 and/or to bathe the tissue at the target tissue. As in the previous embodiments, arms 108, 110 may include a plurality of holes for directing the fluid onto the target tissue, or end holes for allowing convective cooling of electrodes 122. Arms 108, 110 also include thermocouples 134 adjacent to electrodes 122 for providing temperature sensing.

Figure 18A:
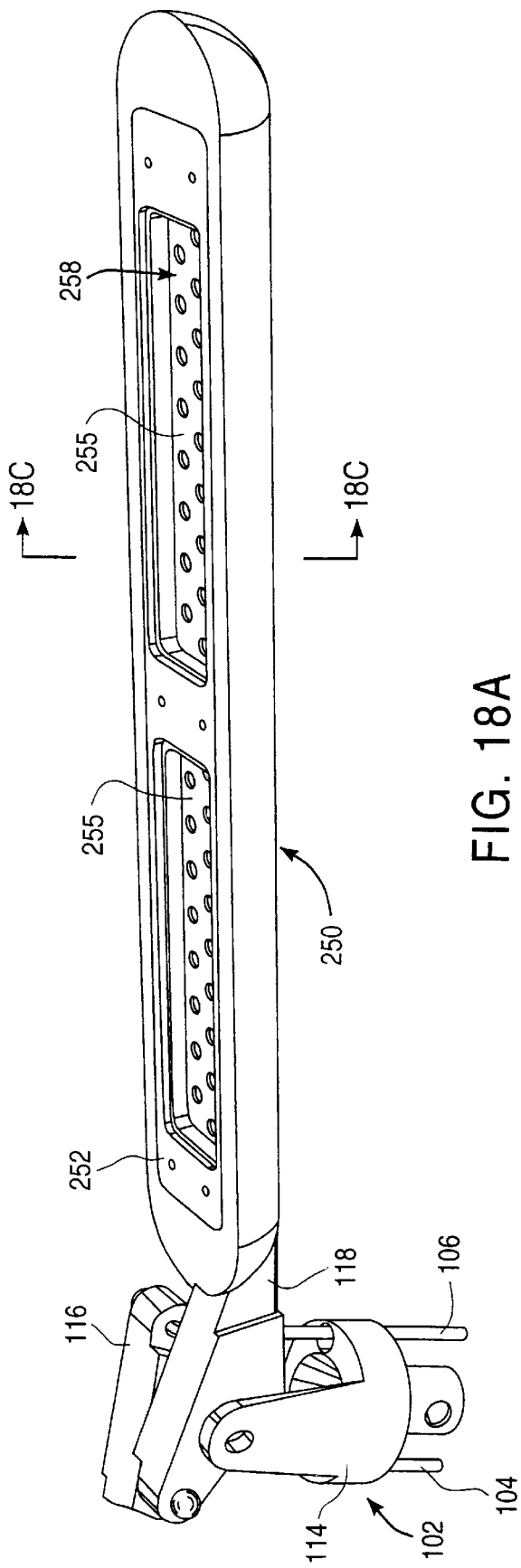
FIG. 18A illustrates another embodiment of one of the arm segments of the catheter of FIG. 1 incorporating a fluid chamber for directing an ionic solution between the electrodes and tissue at the target site.
Figure 18B:
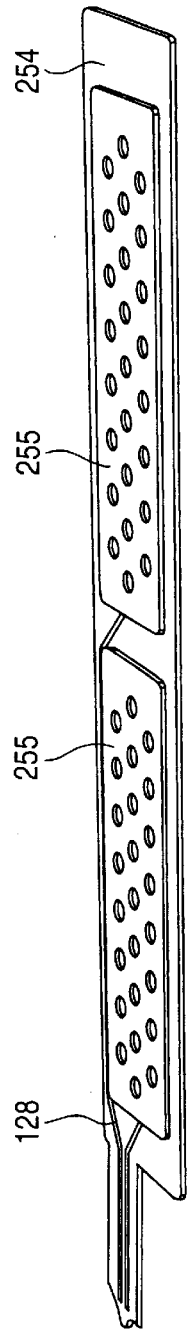
FIG. 18B illustrates an electrode panel for the arm segment of FIG. 18A.
Figure 18C:
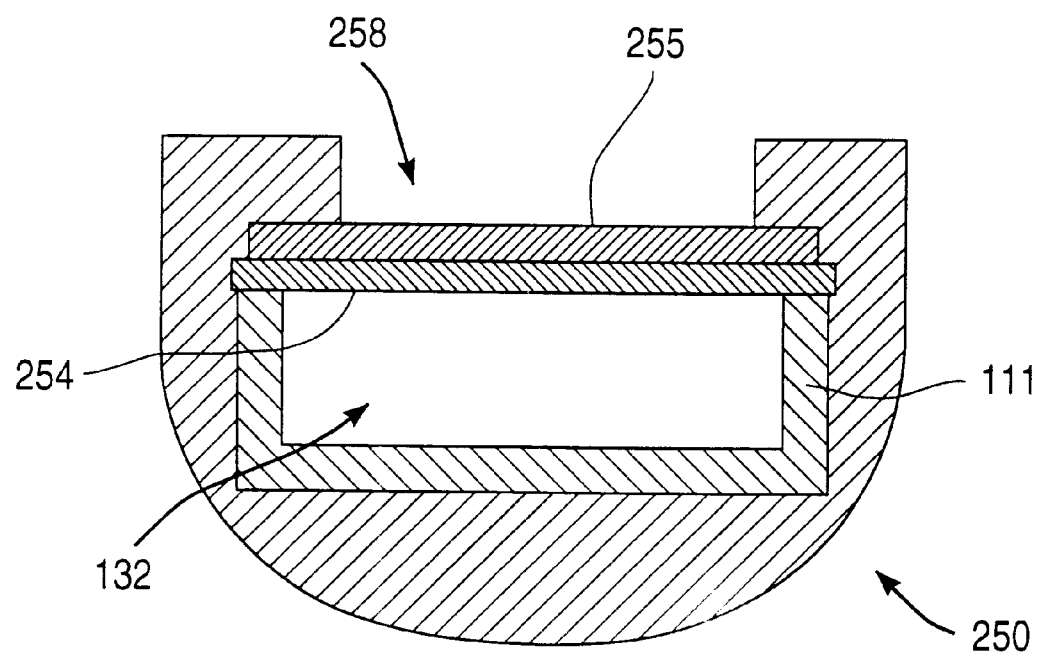
FIG. 18C is a longitudinal cross-section of one of the arm segments of FIG. 18A taken along lines C—C.

Referring now to FIGS. 18A–18C, another embodiment of the ablation assembly will now be described. As shown in FIG. 18A, ablation arm segments 250 preferably have a semicircular cross-sectional shape with a relatively planar contact surface 252 on one side of the arm segment 250. Similar to the previous embodiment, each arm segment 250 will include a fluid plenum 132 (FIG. 18C) coupled to one of the fluid conduits 75, 73 within deflectable tip 28 for delivering fluid to the tissue at the target site. In this embodiment, a flexible circuit 254 is mounted within each arm segment 250. Flexible circuit 254 has one or more electrodes 255 mounted on it with a plurality of openings 256 for fluidly coupling the fluid channel 132 with cavities 258 within arm segment 250. Recessed cavities 258 each provide an interface volume of fluid between electrodes 255 and the target site. In addition, recessed cavity 258 serves to distance the electrodes 255, preferably by about 0.25 to 1.5 mm, to minimize or completely prevent direct contact between the electrodes 255 and the tissue.

The fluid delivered into cavities 258 will preferably be an ionic solution, such as isotonic saline, that conducts electrical current so as to carry the RF ablation energy from electrodes 254 to the tissue. Thus, a fluid interface is created between the electrodes 255 and the tissue to minimize direct contact between electrodes 255 and the tissue and surrounding blood. The fluid interface minimizes overheating and coagulation of the blood, and damage to the tissue. This effectively eliminates the need to remove the catheter and clean the tip after a series of lesions have been formed with the ablation segments 250.

Of course, it should be recognized that this concept of creating a fluid interface between the electrodes and the tissue is not limited to the split tip catheter embodiments described above. For example, the catheter assembly may include a single rigid tip portion with a similar construction as one of the ablation arms shown in FIG. 18A. Alternatively, the catheter may include a flexible tip portion having a plurality of longitudinally extending slots or apertures formed therethrough. In this embodiment, for example, the catheter may include an electrode or electrodes disposed within the distal tip portion of the shaft. The electrode may have holes aligned with the holes of the distal tip portion (which can be an insulating sheath) for allowing fluid to be delivered through the holes to create an electronically conductive fluid interface between the electrodes and the tissue. The fluid, such as isotonic saline, passing through the openings becomes energized with sufficient RF energy supplied by the electrodes to ablate the tissue. A more complete description of this concept can be found in commonly assigned, co-pending application Serial No. Unassigned, "Linear Ablation Catheter", filed concurrently with this application now U.S. Pat. No. 5,919,188, the complete disclosure of which has previously been incorporated herein by reference.

Referring now to FIGS. 13A–13C and 14A–14B, another ablation assembly incorporating a central hinge according to the present invention will be described. As shown, ablation assembly 140 includes a pair of curved flexible support arms 142, 144 extending from the distal end of deflectable tip 28. Support arms 142, 144 are coupled to, or integral with, a linear ablation segment 146 that spans across support arms 142, 144. Linear ablation segment 146 includes first and second movable portions 148, 150 and a central thinned section 152 which is attached to an actuation wire or mandrel 154 to form the hinge point for ablation segment 146. Ablation segment 146 preferably includes a groove 151 extending along its proximal surface for receiving portions of support arms 142, 144. As can be appreciated, axial movement of wire 154, which is suitably coupled to one or both actuator wires 58, 59, causes pivoting of movable portions 148, 150 about thinned section 152. Specifically, withdrawing wire 154 into tip 28 causes the mid-portion of ablation segment 146 to collapse toward the center until movable portions 148, 150 meet along their length in the middle (see FIGS. 14A and 14B). In this manner, ablation segment 146 can be moved from a closed or delivery position (FIG. 14A), in which movable portions 148, 150 are close together and generally parallel to tip 28, and an open or expanded position (FIG. 13A), in which movable portions 148, 150 fold out to form linear ablation segment 146 having a generally planar contact surface 156 perpendicular to the shaft axis.

Figure 13B:
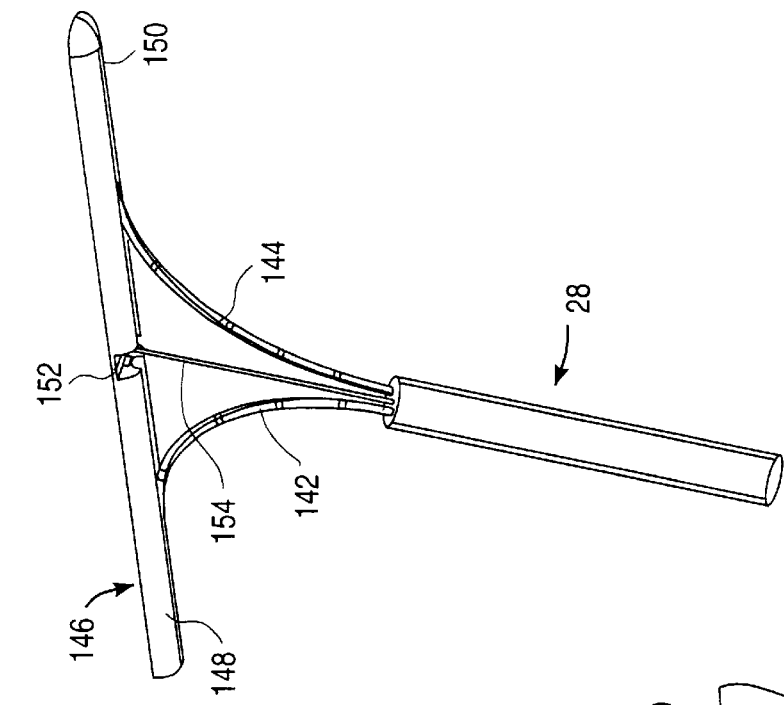
FIGS. 13A–13C are perspective views of another hinge assembly embodiment of the present invention, incorporating a central hinge.
Figure 13C:
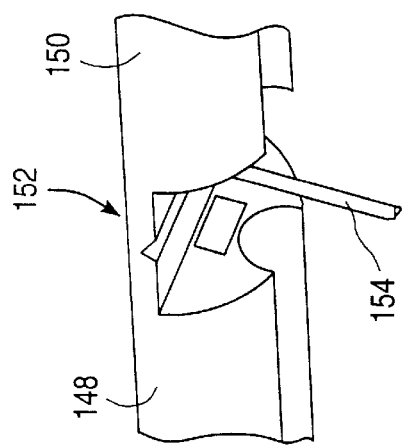
Figure 13A:
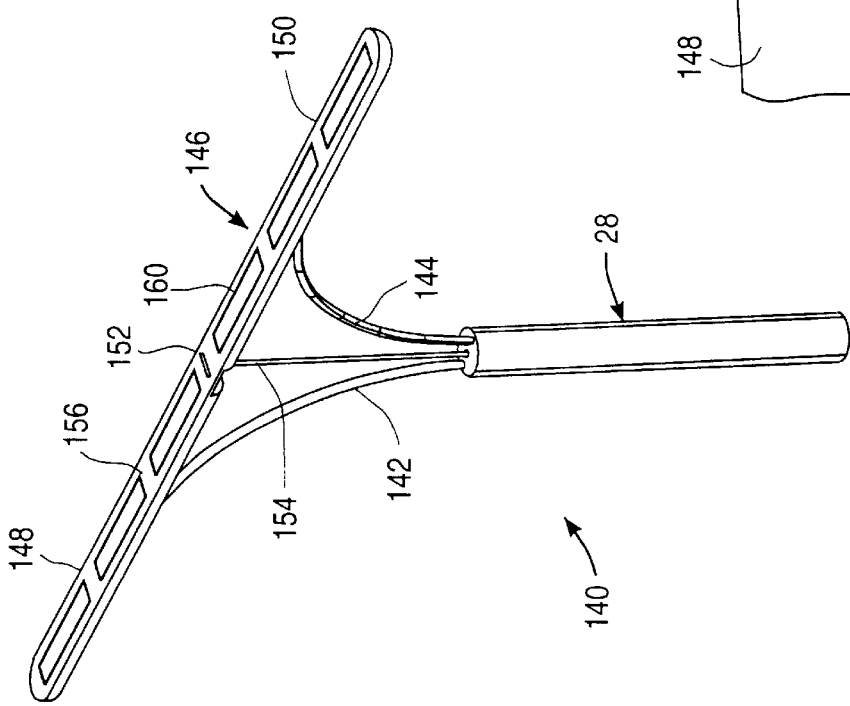

As shown in FIG. 13A, a plurality of electrode pads 160 are disposed on contact surface 154 of ablation segment 146. Preferably, electrode pads 160 and the various electrical/temperature sensor wires (not shown) are snapped into ablation segment 146, which is constructed from a suitable thermoplastic material. Alternatively, the electrodes, sensors and wires may be injection molded into segment 146. The electrical wires extend through the curved lateral support arms 142, 144 of ablation segment 146 to deflectable tip 28 and catheter shaft 6. Similar to previous embodiments, ablation segment 146 may include a fluid channel (not shown) for directing coolant fluid through segment 146 to cool electrode pads 160 and tissue at the target site. The fluid may exit through multiple holes (not shown) in planar surface 154, or through exit holes at the ends of movable portions 148, 150. In the latter configuration, the coolant acts as a heat exchanger, rather than bathing the tissue interface. The fluid is delivered from the catheter shaft to each ablation segment 148, 150 through the support arms 142, 144.

Figure 19A:
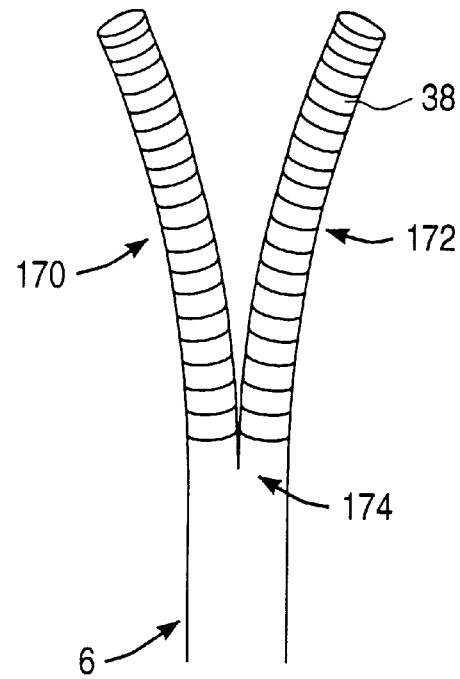
FIGS. 19A and 19B illustrate another embodiment that incorporates a pair of flexible arms that form a Y-shaped distal end.
Figure 19B:
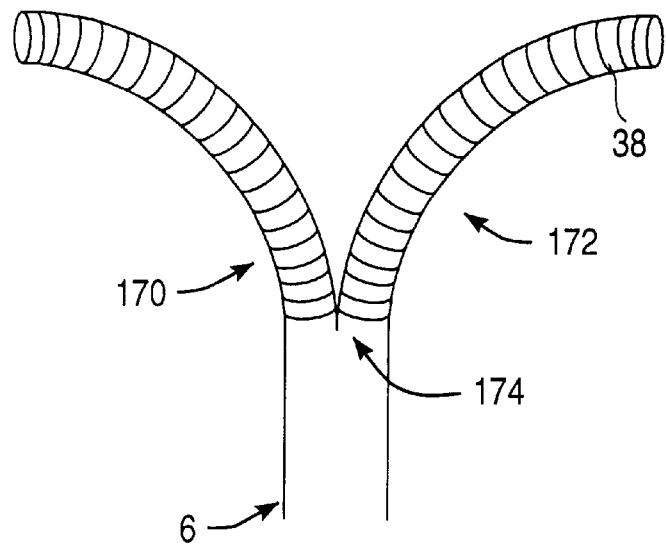

FIGS. 19A and 19B illustrate a modified design of the central hinge assembly illustrated in FIGS. 13 and 14. As shown, catheter shaft 6 has a bifurcated distal end that includes a pair of arms 170, 172 extending away from each other to form a Y-shaped distal end. Arms 170, 172 are preferably biased away from each other into the configuration shown in FIG. 19B, i.e., with arms 170, 172 defining an included angle of about 45 to 90 degrees. Catheter 2 may further include a sleeve (not shown) to urge arms 170, 172 into a parallel configuration for delivery to the target site. Arms 170, 172 are flexible enough to allow pivoting about a central living hinge 174 at their connection point with shaft 6. In this way, the surgeon can push arms 170, 172 against the heart tissue to move them into an open position, preferably defining an included angle of about 120 to 170 degrees, as shown in FIG. 19B. The natural biasing of arms toward the open configuration will facilitate uniform contact with the heart tissue. The arms would be collapsed into a parallel orientation with shaft 6 for removal by pulling back into a delivery sheath (not shown).

Figure 17:
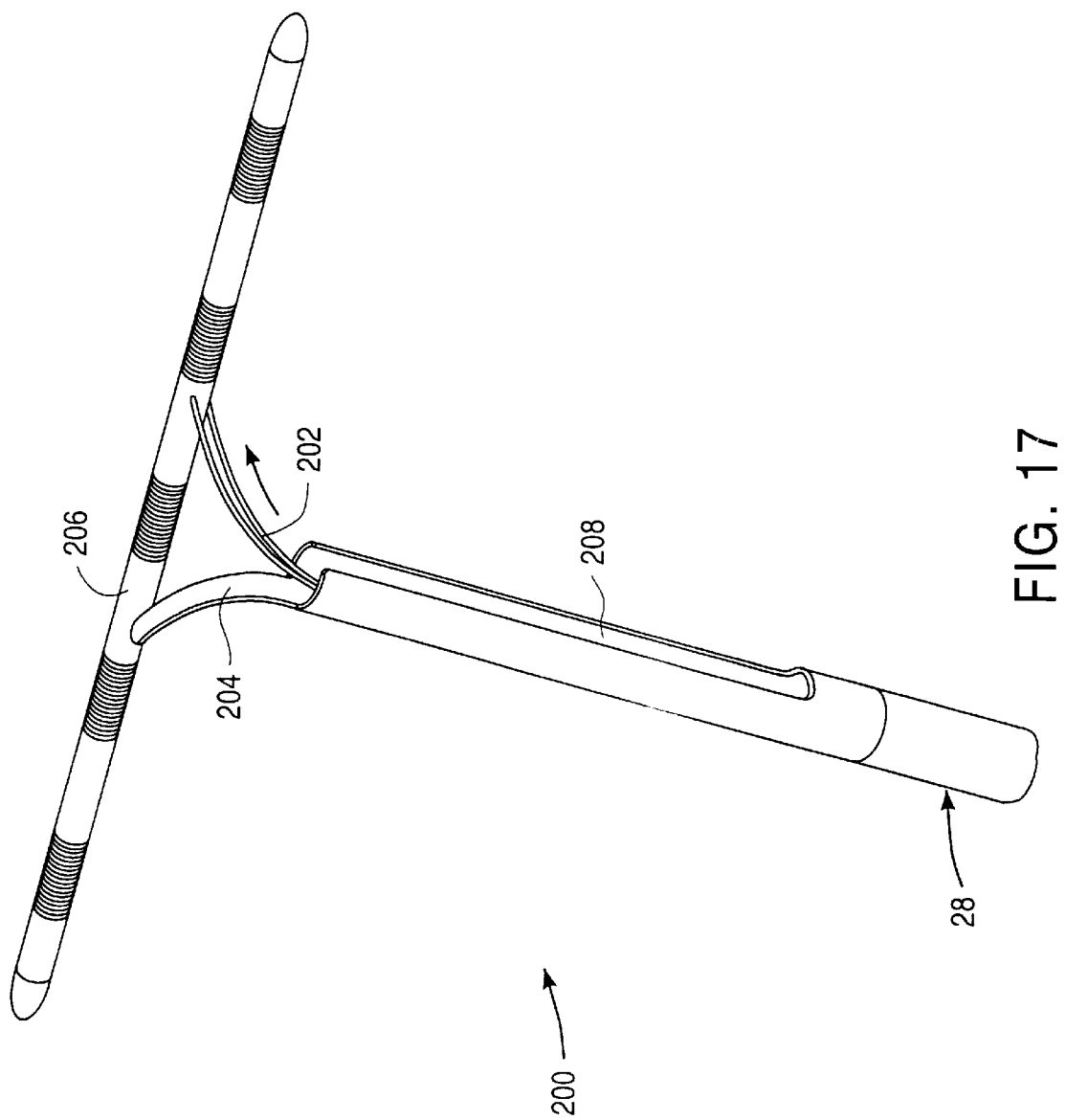
FIG. 17 illustrates yet another embodiment of the hinge assembly of the present invention, incorporating a tilting "cantilever" hinge design.

FIG. 17 illustrates another embodiment of ablation assembly according to the present invention. As shown, ablation assembly 200 includes a curved support arm 204 and a manipulator member 202, such as a wire or mandrel, extending from deflectable tip 28 to a single, continuous linear ablation segment 206. In this embodiment, ablation segment 206 is a continuous member that does not collapse or fold onto itself as in previous embodiments. A plurality of electrodes 210 are coupled to ablation segment 206 as described above. Electrodes 210 may be rings, coils, metallic pads, flattened coils, or any other suitable design. Ablation segment 206 is coupled to actuator wire 58 (FIGS. 2A–2C, only one actuator wire is required in this embodiment) for rotating ablation segment 206 between a delivery position, substantially parallel to deflectable tip 28, and a contact position (FIG. 17) substantially perpendicular to tip 28, where support arm 204 provides the pivot point. In this embodiment, deflectable tip 28 includes a longitudinal opening 208 for receiving ablation segment 206 as it rotates into the delivery position. Thus, proximal retraction of manipulator member 202 causes ablation segment 206 to rotate into opening 208.

Alternatively, retraction of both shafts 202, 204 may withdraw segment 206 into deflectable tip 28. Similarly, distal movement or pushing or shaft 202 causes segment 206 to rotate into the perpendicular or contact position shown in FIG. 17. At this point, a central, symmetric force delivered through catheter shaft 28 on segment 206 maintains a uniform continuous contact with the tissue.

Figure 20:
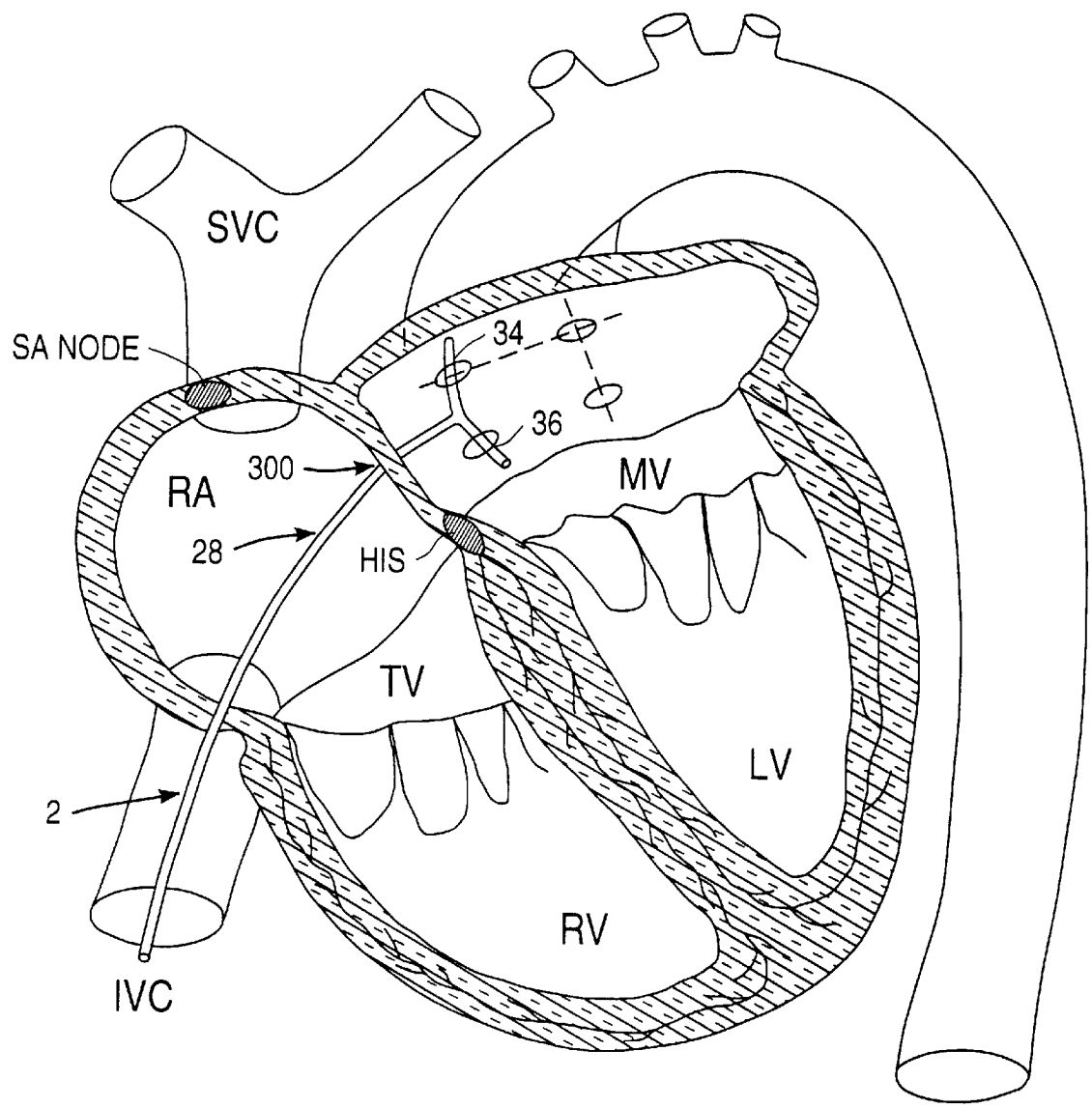
FIGS. 20 and 21 schematically illustrate a method of forming a lesion on the left atrial side of the septum within the patient's heart.
Figure 21:
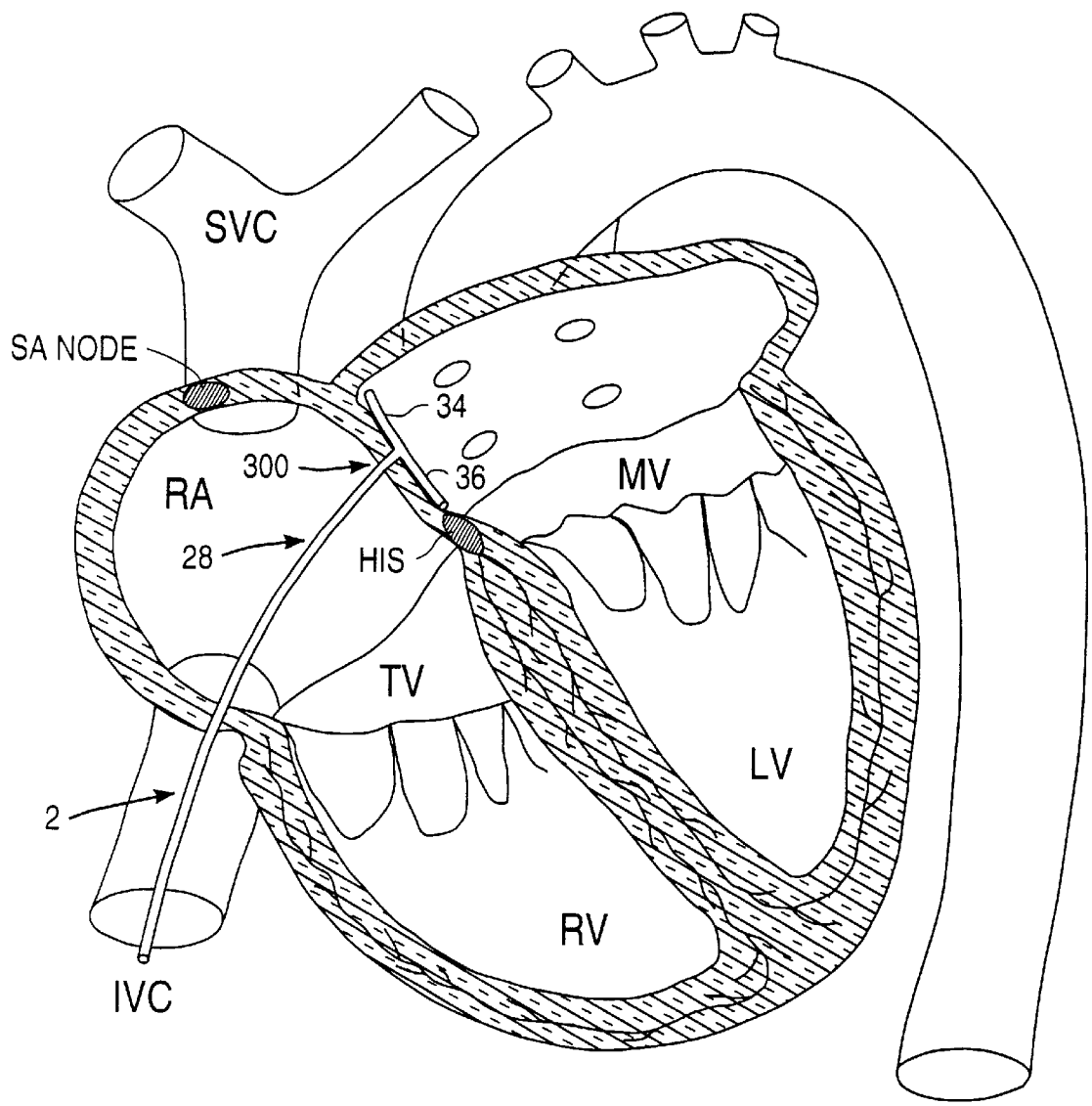
Figure 22:
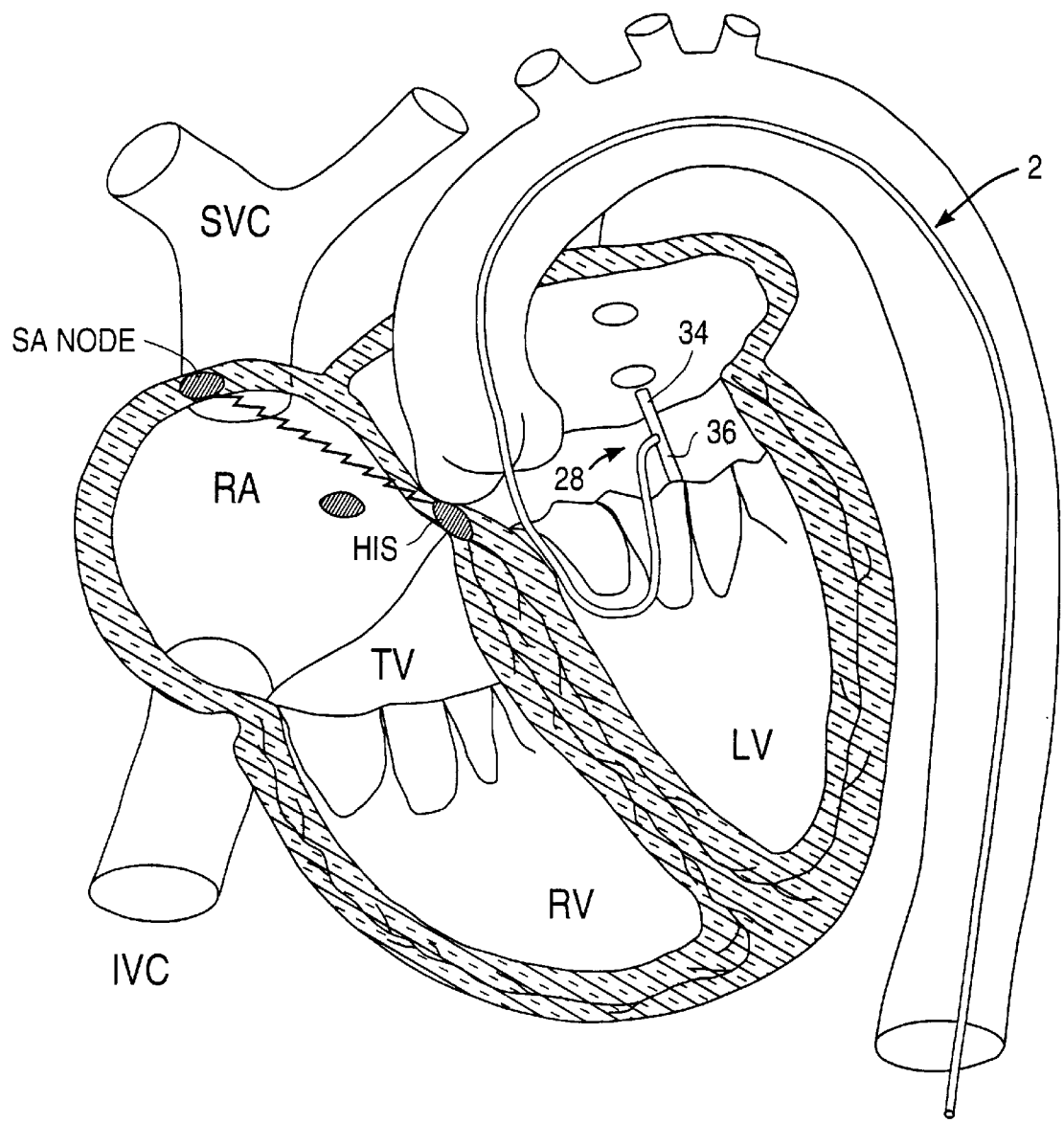
FIG. 22 schematically illustrates a method of forming a lesion across the mitral valve annulus of the patient's heart.

FIGS. 20, 21 and 22 illustrate exemplary methods of creating a substantially linear lesion in the left atrium of the heart according to the present invention. Creating a lesion in this portion of the patient's heart may be desirable, for example, in a catheter ablation procedure similar to the surgical Maze procedure for treating atrial fibrillation or flutter. This procedure typically involves ablating long linear incisions through the heart wall to electrically partition portions of the heart. Ablation arms 34, 36 are collapsed together for percutaneous introduction into the patients vasculature. As shown in FIGS. 20 and 21, ablation arms 34, 36 are endoluminally delivered into the right atrium through the inferior vena cava, and then delivered into the left atrium through a transseptal puncture 300. Once arms 34, 36 are positioned within the left atrium, actuator wires 58, 59 are pulled (or pushed) to open arms 34, 36 as shown in FIGS. 20 and 21. The catheter 2 can then be pushed forward into contact with tissue between the ostia of pulmonary veins (FIG. 20). Alternatively, the catheter can be retracted proximally so that the arms 34, 36 press against the septum, as shown in FIG. 21. It should be noted that the procedure shown in FIG. 21 will preferably be accomplished with circumferential electrodes, such as those shown in FIGS. 3–5, or electrodes mounted to the "backside" of the ablation arms (i.e., the opposite side as that shown in FIGS. 6–10 and 18). Alternatively, a catheter having an ablation assembly as shown in FIGS. 6–10 or 18 may be introduced retrogradely into the left atrium through the aorta via the left ventricle, and then pushed against the desired left atrial location (FIG. 22).

FIG. 22 illustrates another method of using the present invention to make a linear lesion at the ostium of a pulmonary vein or between the pulmonary veins and mitral annulus. As shown, tip 28 of catheter 2 is advanced in retrograde fashion through the arterial system, across the aortic valve, and into the left atrium via the left ventricle. One or both arms 34, 36 are spread open by suitably manipulating actuator wires 58, 59, and the catheter is advanced so that one of the arms 34, 36 cannulates the pulmonary vein and the other arm contacts the atrial wall adjacent the mitral annulus. Alternatively, the arms 34, 36 may be retracted against the mitral annulus to create a lesion between the pulmonary vein and the mitral annulus with the backside of the electrodes. Similar to the above method, the electrodes in this embodiment will either be circumferential, or mounted to the backside of the arms.

Figure 23:
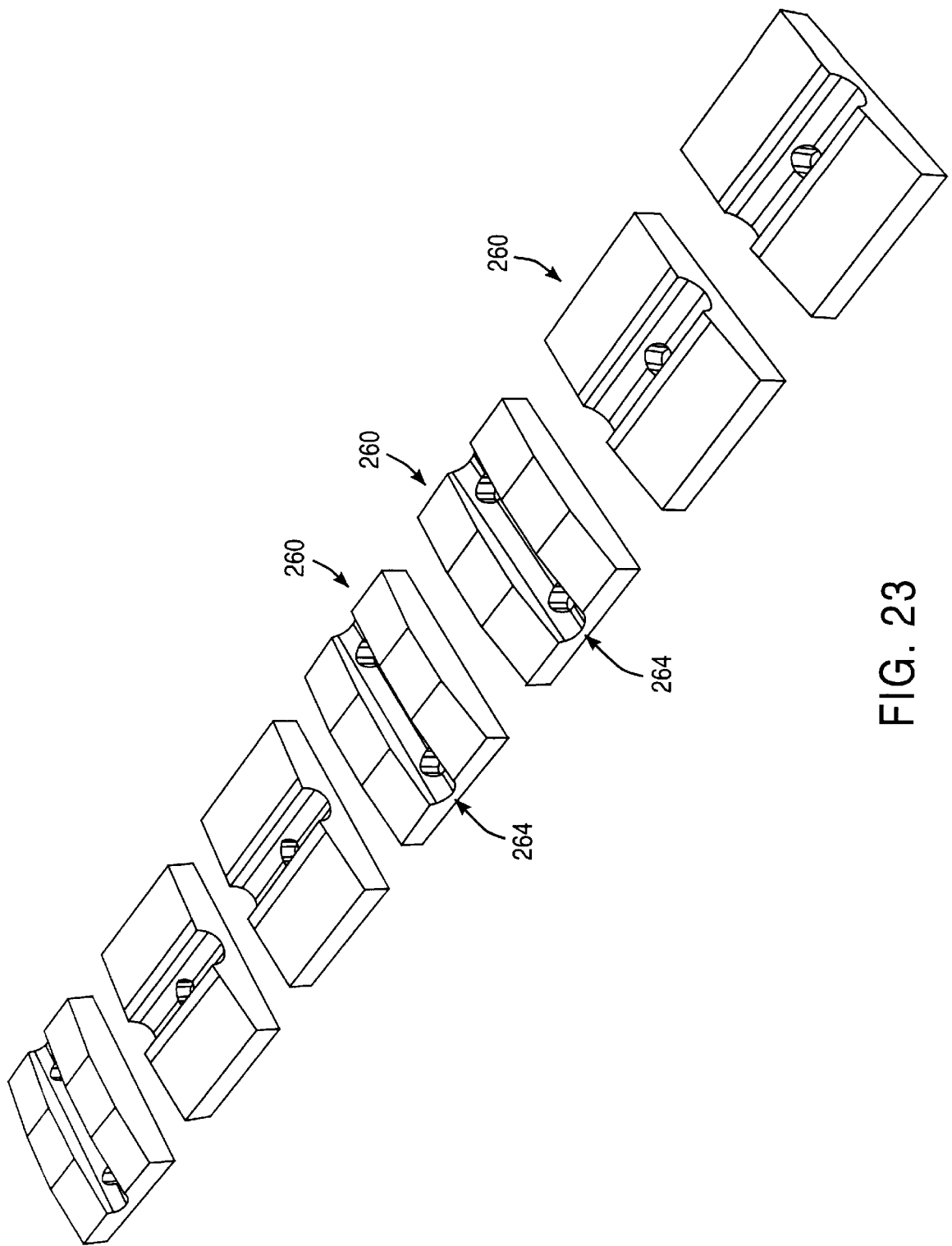
FIG. 23 illustrates an alternative electrode configuration according to the present invention.
Figure 24:
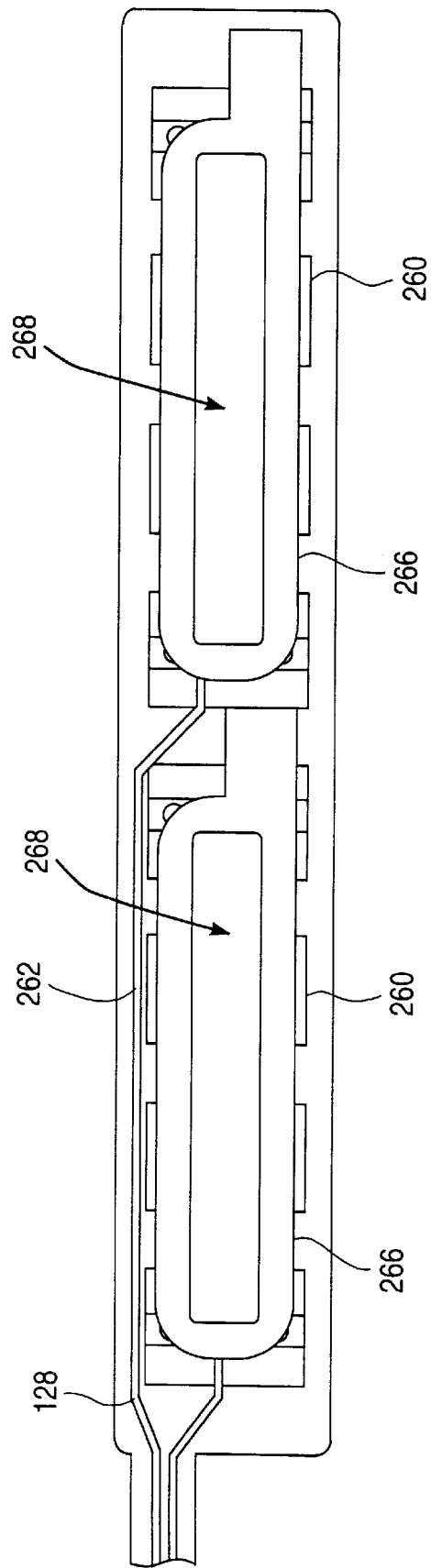
FIG. 24 illustrates a flexible printed circuit for the electrodes of FIG. 23.

FIGS. 23 and 24 illustrates an alternative electrode configuration for one of the ablation segments described above. In this configuration, an array of discrete block electrodes 260 are disposed on an electrode support plate 262. As shown, block electrodes 260 are spaced from each other, and oriented such that grooves 264 formed within the electrodes 260 extend along different directions from each other. As shown in FIG. 24, annular flexible circuit traces 266 extend underneath block electrodes 260 to couple the electrodes to the connectors within the catheter shaft (not shown), as described above. Annular flexible circuit traces 266 preferably have an open interior space 268 to allow fluid flow through electrode blocks 260 to the tissue interface.

What is claimed is:

1. An apparatus for recording electrical signals and/or for applying energy to a target site within a patient comprising:

a shaft having distal and proximal end portions and a longitudinal axis therebetween;

an ablation segment at the distal end portion of the shaft defining first and second opposing ends and having one or more electrodes disposed therebetween;

a connector extending through the shaft for electrically coupling the one or more electrodes to a source of electrical energy;

a force element coupled to the shaft and disposed to apply an axially directed force to the ablation segment between the first and second opposing ends, and the ablation segment comprising a substantially linear arm movable between a collapsed position sized for delivery through a percutaneous penetration in the patient and an expanded position substantially perpendicular to the shaft axis at which the ablation segment forms a substantially continuous surface transverse to the longitudinal axis of the shaft for contacting tissue at the target site.

2. The apparatus of claim 1 wherein the source of electrical energy is a Radiofrequency generator.

3. The apparatus of claim 1 wherein the distal end portion of the shaft has a curvature, the apparatus further comprising an actuator coupled to the proximal end of the shaft for adjusting said curvature.

4. The apparatus of claim 1 further comprising an actuator coupled to the proximal end of the shaft for rotating the ablation segment about the shaft axis.

5. The apparatus of claim 1 wherein the linear arm includes first and second arm segments and an integral hinge therebetween for collapsing the arm segments about the integral hinge.

6. The apparatus of claim 5 wherein the integral hinge is a living hinge, the arm segments being connected together by a thinner portion that allows the arm segments to pivot about the thinner portion.

7. The apparatus of claim 1 wherein the linear arm is pivotable about an axis perpendicular to the shaft axis from a first position, in which the linear arm is substantially parallel to the shaft axis, to a second position, in which the linear arm is substantially perpendicular to the shaft axis.

8. The apparatus of claim 1 wherein the electrodes are divided into multiple segments to improve the flexibility of the electrodes along the ablation segment.

9. The apparatus of claim 1 further comprising one or more temperature sensors coupled to the electrodes on the ablation segment.

10. A steerable electrophysiology catheter comprising:

a shaft having a proximal end, a distal end and an axial lumen therebetween;

first and second ablation segments at the distal end of the shaft each having a plurality of electrodes disposed therebetween, a connector extending through the shaft for electrically coupling the electrodes to a source of electrical energy; and one or more actuator elements extending through the axial lumen of the shaft from the proximal end to the distal end, the actuator elements being coupled to the ablation segments for pivoting the ablation segments into an open position transverse to the shaft axis.

11. The catheter of claim 10 wherein the actuator elements are axially movable within the catheter shaft for pivoting the ablation segments between the open position and a closed position, substantially parallel to the shaft axis.

12. The catheter of claim 10 wherein the source of electrical energy is a Radiofrequency generator.

13. A method for applying energy to a target site in a patient's body comprising:

moving a distal ablation segment of a catheter into an expended position, the ablation segment having first and second ends and the catheter defining a catheter axis, the ablation segment being substantially transverse to the catheter shaft axis when in the expanded position;

the moving step being carried out by pivoting a single, substantially linear arm about a pivot axis perpendicular to the catheter axis from a collapsed position, at which the arm is substantially parallel to the catheter axis, to the expanded position, at which the linear arm is substantially perpendicular to the shaft axis;

contacting tissue at a target site with one or more electrodes on the ablation segment;

applying an axial force to the ablation segment between the first and second ends of the ablation segment to maintain contact pressure between the ablation segment and the tissue; and applying energy to the one or more electrodes and to the tissue at the target site.

14. The method of claim 13 further comprising:

delivering the ablation segment through a percutaneous penetration in the patient; and endoluminally advancing the ablation segment to the target site.

15. The method of claim 13 further comprising:

delivering the ablation segment through an intercostal penetration in the patient into the thoracic cavity; and positioning the ablation segment adjacent the target site on the epicardium.

16. An apparatus for applying electrical energy to a target site on a patient comprising:

a shaft having distal and proximal end portions and a longitudinal axis therebetween;

a substantially linear support arm disposed at the distal end portion of the shaft and having first and second ends and one or more electrodes disposed thereon, the support arm being movable to form a substantially continuous contact surface transverse to the longitudinal axis of the shaft;

a connector extending through the shaft for electrically coupling the electrodes to a source of electrical energy; and a force element coupled to the shaft and disposed to apply an axial force to the support arm between the first and second ends.

17. The apparatus of claim 16 wherein the linear support arm comprises first and second arm segments and an integral hinge therebetween, the first and second arm segments being pivotable about the integral hinge from a collapsed configuration, in which the arm segments are disposed together, and an expanded configuration, in which the arm segments form a substantially continuous line transverse to the shaft axis.

18. The apparatus of claim 16 wherein the linear support arm is pivotable from a delivery configuration, in which the arm is substantially parallel to the shaft for endoluminal delivery to the target site, to an expanded configuration, in which the arm forms a substantially continuous line transverse to the shaft axis.

19. The apparatus of claim 18 wherein the distal end portion of the shaft defines a longitudinal opening for receiving a portion of the support arm in the delivery configuration.

20. The apparatus of claim 18 wherein the force element comprises first and second curved, flexible support shafts extending from the distal end portion of the shaft to the support arm, the support shafts providing a distally directed force against the arm between the first and second ends to maintain contact pressure between the electrodes and the tissue.

21. The apparatus of claim 20 wherein one of the support shafts is axially movable for pivoting the support arm between the delivery and expanded configurations.

* * * * *